US008124845B2

(12) United States Patent
Despeghel et al.

(10) Patent No.: US 8,124,845 B2
(45) Date of Patent: Feb. 28, 2012

(54) FAD-2 MUTANTS AND HIGH OLEIC PLANTS

(75) Inventors: Jean-Pierre Despeghel, Ingre (FR); Christel Granier, Mouguerre (FR)

(73) Assignee: Monsanto S.A.S., Lyon (FR)

( * ) Notice: Subject to any disclaimer, the term of this patent is extended or adjusted under 35 U.S.C. 154(b) by 499 days.

(21) Appl. No.: 12/160,015

(22) PCT Filed: Jan. 4, 2007

(86) PCT No.: PCT/IB2007/001540
§ 371 (c)(1),
(2), (4) Date: Feb. 3, 2009

(87) PCT Pub. No.: WO2007/099459
PCT Pub. Date: Sep. 7, 2007

(65) Prior Publication Data
US 2009/0276911 A1 Nov. 5, 2009

(30) Foreign Application Priority Data

Jan. 4, 2006 (EP) .................................... 06290028

(51) Int. Cl.
A01H 5/00 (2006.01)
C12N 15/82 (2006.01)
C12N 5/10 (2006.01)
C12N 1/20 (2006.01)
C07H 21/04 (2006.01)
C07K 2/00 (2006.01)

(52) U.S. Cl. ........ 800/298; 800/281; 435/410; 435/419; 435/320.1; 536/23.2; 530/370

(58) Field of Classification Search .......................... None
See application file for complete search history.

(56) References Cited

U.S. PATENT DOCUMENTS

| 4,627,192 A | 12/1986 | Fick |
| 5,338,471 A | 8/1994 | Lal |
| 5,773,391 A | 6/1998 | Lawate et al. |
| 5,965,755 A | 10/1999 | Sernyk et al. |
| 6,010,545 A | 1/2000 | Davies et al. |
| 6,312,623 B1 | 11/2001 | Oommen et al. |
| 7,109,392 B1 * | 9/2006 | Broglie et al. ................ 800/298 |
| 2005/0079258 A1 | 4/2005 | Wester et al. |
| 2005/0126071 A1 | 6/2005 | Krull et al. |

FOREIGN PATENT DOCUMENTS

| AT | 397966 B | 1/1993 |
| CA | 2180386 A1 | 1/1998 |
| EP | 0945514 A | 9/1999 |
| EP | 1541664 A1 | 6/2005 |
| EP | 1806398 A | 7/2007 |
| EP | 1862551 A | 12/2007 |
| GB | 642718 | 9/1950 |
| JP | 05039497 | 2/1993 |
| WO | 9115578 A1 | 10/1991 |
| WO | 9411516 A | 5/1994 |
| WO | 9721340 A1 | 6/1997 |
| WO | 9856239 A | 12/1998 |
| WO | 03085070 A2 | 10/2003 |
| WO | 03093403 A1 | 11/2003 |
| WO | 2004072259 A2 | 8/2004 |
| WO | 2006002683 A1 | 1/2006 |
| WO | 2006079567 A | 8/2006 |
| WO | 2006094138 A2 | 9/2006 |

OTHER PUBLICATIONS

Anonymous, "Types of Oils," Internet Article Retrieved Apr. 26, 2005, URL: HTTP://WWW.IASC-OILS.ORG/TYPES%20OF%20OILS.HTM.
Bondioli, P., et al., "Biodiesel Stability Under Commercial Storage Conditions Over One Year," 2003, Eur. J. Lipid Sci Technol., 104:735-741.
Carre, P., et al., "Technological Performances of Low Linolenic/High Oleic Rapeseed Oils for Food and Non-Food Application," Proceedings The 12th Annual Rapeseed Congress, V, Sustainable Development in Cruciferous Oilseed Crops Production, Wuhan, China, Mar. 26-30, 2007, Science Press USA Inc., pp. 152-159.
Corbett, "Research in the Area of High Oleic Oils," 2002, Diversification of Canadian Oilseeds Part 1: Adding Value to the Oil, NRC-PBI Bulletin, 2002, Issue 1, 3 pages.
Friedrich, S., "A World Wide Review of the Commercial Production of Biodiesel," 2004, Institut Fur Technologie Und Nachhaltiges Produktmanagement, 164 pages.
Topfer, R., et al., "Modification of Plant Lipid Synthesis," 1995, Science, 268:681-686.
Brassica Breeding and Research, for Growers, University of Idaho Web Site: http://www.ag.uidaho.edu/brassica/forgrowers.htm, retrieved Jan. 23, 2008, 6 pages.
Database EMBL, EL598 Brassica Embryo Library (EL) Brassica Napus cDNA Clone EL598 Complete, mRNA sequence, 2005. Database Accession No. CN830902.
Setting National Fuel Quality Standards, Paper 6, National Standard for Biodiesel Discussion Paper prepared by Environment Australia, Mar. 2003, Department of the Environment and Heritage, Commonwealth of Australia, 119 pages.
Austrian Biofuels Institute, Report for the IEA, "Biodiesel—A Success Story: The Development of Biodiesel in Germany," Vienna, Austria, Jun. 2001, Update Feb. 2002, 41 pages.
International Search Report Issued in PCT/EP2004/011340, dated Jun. 27, 2005, 3 pages.
International Search Report and Written Opinion issued in PCT/EP2006/062746, dated Sep. 13, 2006, 13 pages.
International Search Report and Written Opinion issued in PCT/IB2006/003847, dated Jul. 26, 2007, 18 pages.

(Continued)

Primary Examiner — Elizabeth McElwain
(74) Attorney, Agent, or Firm — Senniger Powers LLP

(57) ABSTRACT

The present invention relates to plants, seeds and products derived thereof, in particular to *Brassica* plants, seeds products derived thereof, that have mutant sequences conferring high oleic acid profile on the seed oil. More particularly, the invention relates to mutant delta-12 fatty acid desaturase sequences, also referred to herein as FAD2 sequences, in such plants which confer high oleic acid profile on the seed oil.

24 Claims, 4 Drawing Sheets

OTHER PUBLICATIONS

International Search Report issued in PCT/EP2007/052702, dated Sep. 6, 2007, 3 pages.

Office action issued in U.S. Appl. No. 11/571,555, dated Jul. 10, 2009, 9 pages.

Bork, P., et al., "Go Hunting in Sequence Databases But Watch Out for the Traps," 1996, TIG, 12/10:425-427.

Brenner, S.E., et al., "Errors in Genome Annotation," 1999, TIG, 15/4:132-133.

Broun, P., et al., "Catalytic Plasticity of Fatty Acid Modification Enzymes Underlying Chemical Diversity of Plant Lipids," 1998, Science, 282:1315-1317.

Doerks, T., et al., "Protein Annotation: Detective Work for Function Prediction," 1998, TIG, 14/6:248-250.

Fourgoux-Nicol, A., et al., "Isolation of Rapeseed Genes Expressed Early and Specifically During Development of the Male Gametophyte," 1999, Plant Molec Biol, 40:857-872.

Van De Loo, F.J., et al., "An Oleate 12-Hydroxylase from Ricinus Communis L. is a Fatty Acyl Desaturase Homolog," 1995, PNAS, 92:6743-6747.

Database EMBL, "Sequence 12 from Patent EP 1806398," Retrieved from EBI Accession No. EMBL: CS628394, Database Accession No. CS628394, Jul. 19, 2007.

European Search Report and Written Opinion issued in EP 07 29 0043, dated May 19, 2007, 6 pages.

International Search Report and Written Opinion issued in PCT/EP2008/050307, dated May 6, 2008, 20 pages.

Office action issued in U.S. Appl. No. 12/282,696, dated Jun. 15, 2011, 16 pages.

* cited by examiner

| SEQ ID NO 1 | ATGGGTGCAGGTGAAGAATGCAAGTGTCTCTCCCTCCAAAAAGTCTGAAGCGTACCCTGACTGTGGAGAACTCAAGAAAGCAATCCACCGCACTG
TTTCAAACGCTCGATCCCCGCTCTGCTCTTTCTCCTCCTACCTGGTCCACCACTTACTCCCTCTCCCTCCTACTGCCTGGCCTC
TCTACTCGGCCTGCCAGGCTGCCTCGTCTCCTAACCAGTGCGTTCAGCGACTAGCGAGTGCGACGACCAGTGGCTGACGACAAGAGTCAGACATCAAGACCC
GTCCCTTACTTCTCTGAAGTACATCATCGACGCCACCATTGGCTCCTGAGCGTCACTCGACTCTCGGCGGTTCACTCTCCACGCTCGGTCCTAACCCGCGCCTTCACCCCACACGACGTCCAACACCC
TTTGGACGCACCGTGATGTTAACGGTTCAGTTCACTCTCCACGCGCTGGCCATCCTGGCCATGGCCTCGCCGTCTGTCCTGTCCAAGGAGTTGCCTGATGGTCTGCTTCACGAGTTCCTCTTCTGATT
ACGACCGTGAGCGTCTCCAGATATACATTTGATCATTACTTGCAGCACGACGCATCACCTGTCTCGACCATGCCGGATTATACGGATGACGACAGGAAGCGTCGAATCGGAATCTTGAA
GTCAACGGTTCTTAGTTTTTGATCATTACTTGCAGCACGACGCATCACCTGTCTCGACCATGCCGGATTATACGGATGACAAGCGGTACGAAGCTGAAGGCCATATTAAAGGAGAATCTTGAA
CAAGGTCTTCCACAATATCACGGACAGGACAGCGAAGCACAGCAGTGTATCTATGTGGAACCGAAGGTGAAGGACAAGACGAAGGGAGACGACATAAGAAG
CGCCGGTGGTTAAGGCGATGGAGGCAGGCCAAGGCGTGATCTATCAGGCAAGGTGAACCGAACAATAAGTTATGA |
| SEQ ID NO 2 | MGAGGRMQVSPFSKKSEIDNIKRVPCETPFTVGELKKAIPPHCFFKRSIPRSFSYLIWDIISACFYYVAIYPLLPHELSYFAWPLYWACQGCVLTGVWIRAECDHHAFSDYQWLDDTVGLIFHSFLL
VPYFSWKYSHPRHHSNTGSLEPDEVFVPKKKSDIKWYGKYLNNPLGRTVMLITVQFTLGWPLYLAFNVSGRPYDGGFACHFPMAPIYNDRERLQIYISDAGLLAVCYGLYRYAAVQGVASMVCFYGVPLLI
VNGFLVLITILQHTHPSLPHYDSSEWDWLRGALAIVDRDYGILNKVFHNITDTHVAHHLFSMPHYHAMEATKALKPILGEYYQFDGTPVVKAMWREAKECIYVEPDRQGEKKGVFWYNNKL |
| SEQ ID NO 3 | ATGGGTGCAGGTGAAGAATGCAAGTGTCTCTCCCTCCAAAAAGTCTGAAGCGTACCCTGACTGTGGAGAACTCAAGAAAGCAATCCACCGCACTG
TTTCAAACGCTCGATCCCCGCTCTGCTCTTTCTCCTCCTACCTGGTCCACCACTTACTCCCTCTCCCTCCTACTGCCTGGCCTC
TCTACTCGGCCTGCCAGGCTGCCTCGTCTCCTAACCAGTGCGTCATAGCGCCACCTTCAGCGACTGCGACGACCAGTGGCTGACGACAAGAGTCAGACATCAAGACCC
GTCCCTTACTTCTCTGAAGTACATCATCGACGCCACCATTGGCTCCTGAGCGTCACTCGACTCTCGGCGGTTCACTCTCCACGCTCGGTCCTAACCCGCGCCTTCACCCCACACGACGTCCAACACCC
TTTGGACGCACCGTGATGTTAACGGTTCAGTTCACTCTCCACGCGCTGGCCATCCTGGCCATGGCCTCGCCGTCTGTCCTGTCCAAGGAGTTGCCTGATGGTCTGCTTCACGAGTTCCTCTTCTGATT
ACGACCGTGAGCGTCTCCAGATATACATTTGATCATTACTTGCAGCACGACGCATCACCTGTCTCGACCATGCCGGATTATACGGATGACGACAGGAAGCGTCGAATCGGAATCTTGAA
GTCAACGGTTCTTAGTTTTTGATCATTACTTGCAGCACGACGCATCACCTGTCTCGACCATGCCGGATTATACGGATGACAAGCGGTACGAAGCTGAAGGCCATATTAAAGGAGAATCTTGAA
CAAGGTCTTCCACAATATCACGGACAGGACAGCGAAGCACAGCAGTGTATCTATGTGGAACCGAAGGTGAAGGACAAGACGAAGGGAGACGACATAAGAAG
CGCCGGTGGTTAAGGCGATGGAGGCAGGCCAAGGCGTGATCTATCAGGCAAGGTGAACCGAACAATAAGTTATGA |
| SEQ ID NO 4 | MGAGGRMQVSPFSKKSEIDNIKRVPCETPFTVGELKKAIPPHCFFKRSIPRSFSYLIWDIISACFYYVAIYPLLPHELSYFAWPLYWACQGCVLTGVWIAHECGHHAFSDYQWLDDTVGLIFHSFLL
VPYFSWKYSHPRHHSNTGSLEPDEVFVPKKKSDIKWYGKYLNNPLGRTVMLITVQFTLGWPLYLAFNVSGRPYDGGFACHFPMAPIYNDRERLQIYISDAGLLAVCYGLYRYAAVQGVASMVCFYGVPLLI
VNGFLVLITILQHTHPSLPHYDSSEWDWLRGALAIVDRDYGILNKVFHNITDHVAHHLFSTMPHYVHAMREAKECIYVEPDRQGEKKGVFWYNNKL |
| SEQ ID NO 5 | ATGGGTCAGGTGAAGAATGCAAGTGTCTCTCCCTCCAAGAGTCTGAAGCCGACACCGACATTAGCCTGGAGAACCGACACCGCTCGTCTACCCTGCGAGAACTCAAGAACAATCCCACCGCACTG
TTTCAAACGCTCGATCCCTCGCTCTGCTCTGCTCTGCTCTGCTCTGCTCTGCTCTGCCTACGTCTGCTACCTGCCTCCATCATCGCTCGGCTCCTGCCTGCCTCTCTCTCTCTCTC
TCTACTCGGCCTGCCAGGGTCGTCCTAACCCAGTGCCTTGGCGTCATAGCGCCACCACTGGCTGACGGCTCAGTGGTTGCTTGAGACCTTTCTCCACCTCCTCCTCCACTCTTCCTCTCCTC
GTCCCTTACTTCTCTGAAGTACATCGACGCCACCACCATTGGCTCCTGAGCGTCACTCGACTCTCGGCTTGTACTTTGACAAACGGCAAGTCGGTACGGCAAGTACCTCAACAACCC
TTTGGACGCACCGGAGCGTCTCCAGATATACATTCGACGCGTTAAGCTCTTCCCGTCTTCACTCTTCCCTCGCGTCGGCATCTCGGCTGGCGATCCTGCATGGCCGCAGGGGAGGCGCTTCGATGGTCTGCATGGTCTGCTTCTCGATG
GTCAATGGTTCTTCCACAATATACCGACACGACGTGTATCGTACTGGAAGGAGCAATCATCCGTCCCACGGCATCATCGTCCGATGCGAAGTCCGATGAAGGTGAACCGAAAGACCCGATAAAAGCCGATGAAGACCTTGGCCTTTGGCTTTGCTCTGGAGGCAGCTTCGGCGAGAGTATCACTAAGCTTGACA
CGCCCGGTGGTTAAGGCGAATGCGAGGGAGGCCAAGGCGTGATCTATCAGGCAAGGTGAACCGAAGAAGAAGGTGTGTTCTGGTACACACAATAAGTTATGA |

| SEQ ID NO 6 | MGAGGRMQVSPPSKKSETDTIKRVPCETPFTVGELKKAIPPHCFKRSIERSFSYLIWDIIIASCFYYVATIYFPLLIPHPLSYFAWPLYWACQGCVLTGVWVIAHECGHHAFSDYQWFDDTVGLIFHSFLL<br>VPYFSWKYSHRRHSNTGSLERDEVFVPKKKSDIKMYGKYLNNPLGRITVMLTVQPTLGWPLYLAFNVSGRPYDGGFACHFHPNAPIYNDRERLQIYISDAGILAVCYGLFRYAAAQGVASMVCFYGVPLLI<br>VNGFIVLITYLQHTHPSLPHIDSLRGALATVDPDYGILNKVFHNITDIHVAHHLFSTMPHYHAMEATKAIKPILGEYYQFDGTPVVKAMWRRAKECIYVEPDRQGEKKGVFWYNNKL |
|---|---|
| SEQ ID NO 7 | ATGGGTGCAGGTGGAAGAATGCAAGTGTCTCCTCCCTCAACCATCAAGGCGTTGAAACCGACACATCAAGGCGGTACCTGTGAGACTCCCCTTCACGTGTGGCGAGACTCAAGAAAGCAATCCCACCGCACTG<br>TTTCAAACGCTCGATCCCTGCATTCCTCTACCCATCTATGGACATCATCAGCCTCCTGCTTCTACACGCGCCTTACTGCCTCTCCCTCTCCACCTGTGGCGTCACTCTTCACTCTTCCTCTC<br>TCTACTGGGCCTGCCTCGCCTTGCAACAGATCTACGTTAACGACCAGCACGCCATTCCAACACTGGCTCTCCAGAGAAGTCAGACATCAGTGCTACGGCCAAGTAGCCTGACAACCC<br>GTCCCTTACTTCTCCCGTCAAGTACAGTCAGGTTTCAGTTCACTCTCCGACGGTCTCAACCTCTCCGGGAGACCCTTCAACCTGCGAATCCACCCCAACGGCTCCCGCTTCTACA<br>ACGACCGACCAGGCGTCTCCAGATATACAATCCGACACGCAATCTCTGCTTCCTCTACGACTGTGACGACGACTAAGCCGCCGCGAGGAAGTGGTTGAGGGAGCTACCAAGGCGATAAAGCCGATACTGGGAGGACTTGTTATCCAGTTGTGATGCGA<br>CAAGGTCTTCCACATTACCGACACGCTGTCGAGGCGATCCGATTGTATCTATCGGAACCGACAGGCCAAGCGTGAGGACAAAGGCGTCGTTCTGGTACAACAATAAGTTATGA<br>CGCCGGTGGTTAAGCCCATCGAGGGAGGCCCGGATCTATCTATCTATGCTAGAACCGGACAGGCCAAGCTGAGAGGACAAAGGCGTCGTTCTGGTACAACAATAAGTTATGA |
| SEQ ID NO 8 | MGAGGRMQVSPPSKKSETDTIKRVPCETPFTVGELKKAIPPHCFKRSIERSFSYLIWDIIIASCFYYVATIYFPLLIPHPLSYFAWPLYWACQGCVLTGVWVIAHECGHHAFSDYQWLDDTVGLIFHSFLL<br>VPYFSWKYSHRRHSNTGSLERDEVFVPKKKSDIKMYGKYLNNPLGRITVMLTVQPTLGWPLYLAFNVSGRPYDGGFACHFHPNAPIYNDRERLQIYISDAGILAVCYGLFRYAAAQGVASMVCFYGVPLLI<br>VNGFIVLITYLQHTHPSLPHIDSSEWDNLRGALATVDRDYGILNKVFHNITDIHVAHHLFSTMPHYHAMEATKAIKPILGEYYQFDGTPVVKAMWREAKECIYVEPDRQGEKKGVFYWNKL |
| SEQ ID NO 9 | GAGAACCAGAGCAGAGATTCATTACCAAAGACGATAGAGCAGAGAAGATGAGGAGACAGAGAGAGGAGACAGTTTGAGAGGAGGAGCTTCTTCCGAGACGCCTATCCTGTCGAGAACTCAAGAAA<br>CAGCCAGCTCAAGAACATGGTGCAGGTCGAAGAAATGCAAGTGTCTCGTCTTCTCCTTACCCATCTGAAACCGACACGACAATAGCCTCCTGCTTCTACACGCCTTACTGCCTCTCTC<br>GCAATCCCACCGCACTGTTTCAAACGCTCGATCCCTGCATCCTCTACCCATCTATGGACATCATCAGCCTCCTGCTTCTACACGGTGTGGCGTCATAGCCGGCATCGAAGCCGGGAC<br>CTACTTCGCCTTGCCTCTCCGCTTCCTCGTCCCCTTACTTCCCAGAGCAGACTGAACTCAACTCGTCACTCATCCGGCTTGACGTTAAGCGCTCTCCAACGATCATAACCGCTCACGCCGCACGTGCAGGATCAGATGTCATGAGTCAAAAACCGACACGATC<br>TCCACTCCTCCCTCCCTCGTCCCTTACTTCCCGTCCCCATTCGAACTGAGTCGAGACTCAGCACGGGACTTGCCATTCCACCC<br>AAGTACCTCAACACCCCTTGGGACGCACCGTGATCGGTTTAAACGGTTCAGCTTCACTCTGTCCTGTCTTAAGCCTCTGGAGGTTTCTCGGGGAGCCTGCCTCTGATGGCTGCACCAACGTTGCTATGCCAAGGAGTATACCTTCCACCC<br>CAACGCTCCCATCTACAACGACCGTGAGCGTCTCCAGATATCACATCCGACACGGCCATCCTCAACACGCATCTACTTCCGACTACTTCCAGCACACGCATCACCTGTTCTGACCATCATCGCGCTTTATCATGCCGATAAAGCCCATACTGGGAGAGTA<br>GAGTTCCTCTTCGATTGTTACCGGGTTCTAGTTTTGATCACTTACTTCCACAATATCACGGACACGCCATCGCGGACACATGAATATCATCGCGACGAAGAAGCTACGAAGGCCGATAAAGCCCATACTGGGAGAGTA<br>GACTACTCGGAATCTTGAAACTGTTTTCTCGTTCCGGTCACGGTTTCAACGGTTTCCGCCAAAAAGGGCTTGGATCAGATTGTTTCTTTGTCCGTTCCGCATCCAAGGTTATCATCAATCTTAATTATCCAATATTCCAAGCTTGTGTTTGACATTGTGACATTGTGATGCGAATGTGGAAAGTT<br>AAGAACTGAACCTTTCTCTCTCTATGCGCATCGTCTTCTCTCATCGATCGTATTGTTTGGAATCGTTGAAAATGGACATTTCGGACTAGTGAACCTCTTGTCTGAACTAAAAAAAAAAAAAA<br>AGTGTCTAAAATGTCTTCTGTCTCTATGATGTTCTTCTCTCATCGATCGTATTGTTTGGAATCGTTGAAATGGACACTTGGACTAGTGAACCTCTTGTCTGAACTAAAAAAAAAAAA |

| SEQ ID NO 10 | GAGACAGAGATTCATTACCAAAGAGATAGAGAGAAAGAGAGAGAGAGAGAGTGAGTTTGAGGAGGAGAGCTTCTTCGTAGGGTTCATCGTTATTAACGTTAAATCTTCACCCCTACGTCAGCCA<br>GCTCAAGAAACATGGGTGCAGGTGGAAGAATGCAAGTCTGTCCCCTCCCAAGAGAGTCTGAAAACCGACACCATTCAAGGCGTACCCTGTGAGACACCGCCCTTCACGTGTGGAGAACTCAAGAAGCAATC<br>CCACCCCACTCGTTTCAAACGCTCGATCCCTCGCTCTTCTCCTGCATCATCATAGCCCCTCCTCCTTCTGGACATCATAGCCCCTCGTCGCCACCACTTACTTCCTCCCCCCTACCCTCTCCCTACTT<br>CGCCTGGCCTCTCTACTGGGCCTGCCAGGGTGCGTCTGGGTCATAGCCCAGAGTGCGGCCACCAGAGTGGTGCTGTGACGACTACCAGTTGTGACACACGACTACCAGGTCGGCTCTCATCTTCCACT<br>CCTTCCTCCTCTCGTCCTCTACTTCTCTGGAAGTACAGTCAGTTCATGATCAATCGGTTAAACGGTTCACTCTCGACCTTGTACTTAGCCTCTCACGTCTCCCAAGAAGAAGTCAGACATCAAGGTGTACGGCAAGTAC<br>CTCAACAACCCTTTGGGACCCCGACCGTCTCCAGAGTACCGTCCAGGTCCAGATACATCTCCAGATATCATCTCCAGATGGTTCTCCTGTTACTGACGACCTTACGACCCTCTCCACCCCCAAGCGC<br>TCCCATCTACAACGACCGCGAGCGTCTCCAGATACACTCCCAGATATCTCCAGATGGTCTGTCCGTTCTCCCGTTACGGCGCGGSCAGGGAGTGGCCTCGATGGTCTCTCTACGAGTCC<br>CGCTTCTGATTGTCAATGTTTCCTCGTGTTGATCACTACTTGCAGCACACGCATCCTTCCCGTCTCACGATCCGCATTATCACGCAGGAGATAGCTACCAAGGCGATAAAGCCGATACTGGGAGAGTATTATCA<br>GGAATCTTGAACAAGGTCTTTCCACAATATTACCGACACGAGGAGCGAATGGAGGAGCGGAAGGCGTATCATGTGAACCGACAGGGAGAAGAAGGTGTGTTCTGACATTTTGTTTCTGACATTTTGGCTAAAATTATGTGAAGTTAGTGTCTA<br>GTTCGATGGACGCCGGTGGTTAAGCGACGATGGAGGAGGCGGAAGGAGCTATGTTCTGTCGTTTCAATTGGAACGACAAGGTGTATCATGTGAACCGACAGGGAGAAGAAGGTGTGTTCTGACATTTTGTTGACATTGTGAAGTTAGTGTCTA<br>TGAACCTTTCTCTCCTATGATTGTCTTGTTCTCATCGCTGTATGTTTGGGATCGTGTTCAAATGACTTTCGGACTAGTGACTTTGTCCTCGAACTAAAAAAAAAAAAAA<br>AAATCTCTTGTGTCTGTATTGTTCTTCTTCATCGCTGTATGTTTGGGATCGTGTTCAAATGACTTTCGGACTAGTGACTTTGTCCTCGAACTAAAAAAAAAAAAAA |
| --- | --- |
| SEQ ID NO 11 | AGAGAGAAGAGGAGACAGAGAGAGAGAGTTTGAGGAGGAGCTTCTCGTAGGGTTCATCGTTATTAACGTTAAATCTTCAtCCCCCCTACGTCAGCCAGCTCAGGTCCCTTCTTCTTCCATTCTT<br>CTCATTTTACGTTGTTTCAACTGGCTCTGTTCTTTCTTATCGCTTTCGTTCTGTCTATCATCATTTTGCATTCTAGATCTGTTAATTATTATTGCATTAAACTATAGATCTG<br>GTCTGATTCTCGTTTCATCGTGTGAAATCTTGATGTGGTTGGTGGAGTTGAATCTTGAAAAATCACCATAGCAGTCTCCTGGTCTAACCATTAATGTCTATAACCGTGGAGAATACAGAGTGTTGCATTTGTCCGAATACAAACTGTTGACTTTC<br>AATCGTTTTAAAATTATATATATTTTGATGGGTTGGTGGAGTTGAATCTTGGGTAAAACTTATGTCTCTGGTAAAATTTGCTGAGAGATTTGACCGATTCTATTGGCTCTGAGATCGATATGGAAATTAAGGATTCATGA<br>TAGAATCTGGACCTGAGACATGTAAGCTACATGCCTATGCTCACTTCATGCTTATCACTTTATAAACTTATTCTTGCAATTAATTGGAATTAAGATTATTGCAAATTATTAGGATTCAGATTGCATGAAGATGAAGAAATAATAGGATTCATGA<br>ATGAAAAACTTTCATTGGCCTAGCCAAGTGACATGTAAGCTACATGCCTATGCTCACTTCATGCTTATCAGTTTCGTTCATTTAGGTTTATGTTTTGTCAAGTTGCTTATTCTAAGAGACATTGTGA<br>TAGTAAAAAGATTGTATTTTGTTGTTTGTTAATAAAGACGAAAGAAATTGATATCCACACAAGAGAGAGTGTAAGCTGTAACGTATCAAATCTCATTAATAACGTAACACTGAATATAAATTGTTGGTTA<br>TTATGACTTCTCTCTCTAACGTAGTTTAGTAATAAAGACGAAAGAAATTGATATCCACACAAGAGAGAGTGTAAGCTGTAACGTATCAAATCTCATTAATAACGTAACACTGAATATAAATTGTTGGTTA<br>TTTCTTTCTTGGTTTGCCACTATATGCCCGCTTCTCTCTCGCTCTTATCCAGAAACAATGGGTGCAGGTGCAAAACATGCTGAAAGATGGAAGATGCAAGGGCTCCTGCGTGAGACACCGCCCTTC<br>ATTAACTTTGAGTCTTTGCTTTTGGTTTATGCGAGAACAATGGGTGCAGGTGCAAAACATGCTGAAAACGCTGAAAACATCAAGCCGCGTCTTCTACTTCCTCGTCCACCACTTACTTCCC<br>ACTGTCCGAGAACTCAAGAAGCAATCCCCACCGCCACTCGTTTCAAACGCTCGATCCCCTGCCTCTTCAAACGCTCCGATCCCTCCGATCCCCTGCCTCATCGGCAGATCGGGGCTGGGGCTCATAGCCCACGAGTGCGACCCCACCACCACCAGTGGCTGG<br>TCTCTCCTCCCTCCCCACCCCTCTCCTCCTGCACCCCTTCCACCTCTTCCACTCTTCCACTCTTCCCTCCTACTTGGCCTCTAGAGTCATGACGGCCACCATTCCAAACTACGGCCCTTTGTACTTAGCCTTCACGTCTGGAGAGGACCTTCAAGCTGTTGGAGACCTTGTCCAAGGAGAAGTTG<br>ACGACACCGTCGGCCTCATCTTCCACTCTTCCCTCCTACTTCGTCTTGGGACGACACCGTGATGTGACGGTTCAGTTAACGGTTGAACCGGTTGAACGGTCTCCAGATACATCTCAAGCTGTTCGTTCACTGCCGTCGGCACCATTAGCCTTACGCTGGTTCACGTCTAGCTGTTGATCCTTGGGAGACCTTGTCCAAGGAGTTG<br>CTTCGCTTGCCATTTCCACCCCAACCGTCTCCAATCTACAAGACACCGTGAGCGTCTCCAGATACATCTCAGATACATCTCCGATGTCCCCGATGTTTGATCATCCACCGTCCGGCATCCTCGCCGTCTGTCCTCGCTCTGCCTCACTATGATCTGGTTCACGTCTTCAAGGTGAGGACCTTGTCCAAGGAGTTG<br>CCTCGATGGTCTGCTTCTCTACGACGTGAGTTCAGGTTCTTTAGTTTTGATCATTACGGACACAGGTCTTCCACAATATCACGGACACAGCCGGGCCATTATTCATCATGTGCCGCCAATATCATGGCCAATATCACGACCAAGGGTGTCAAGCGATGCAAAGGTAGGATGGGGA<br>GCTTTGGCCACCGTTGACAGAGACTACGGAGTCTTCTCACAGAGTTCTCCACAAATATCACGGACACAGCCGGGCCATTATTCATCATGTGCCATTATCACGACCAAGGTGTATCATGCACCAAGGGGTGTCATGACGAAGCATGGAAGGTGAAGGGGGAT<br>AAAGCCGATACTGGAGACGATATCGCTATTATCAGTTCGATGGAGGCTCACAGAGACATGCATCTGTTTATGAAGCTGGAAGCTATGTCTTCTGGAAGAATGCATGTCTGTTCGATCAGTGACTATCAAGCCGACCAAGCTGGAAGCTATGTCTTCTGGTTCGATCAGTGACTATCAAGCCGACTATCATTCAATAATCATTTAATTATCATTTTGTGTTATGTTTGGGATCCTGTTATGTTGGGACTAGTGACTTTGTGCCTGGTACA<br>ACAATAAGTATCGATGTGGAAGTTAGTGTCTAAAAGCAAAGAAAGAAACTGAACCTTCCATCGATCTGTGTCTGTATGTTTGGGATCCTGTTATGTTGGGACTAGTGACTTTGTGCCTGGTACA<br>AATTATGTGATGTGGAAGTTGGAAGTAGTGTCTAAAAATGTCTAAAATGTCTGTTTAATATGCTTAATTATCATTTTGTGTTTATGTTTGGGATCCTGTTATGTTGGGACTAGTGACTTTGTCCGAACT |

| SEQ ID NO | |
|---|---|
| 12 | GAGAAGAGAGAGAGAGAGAGAGAGAGTGAGTTTGAGGAGGAGAGCTTCTTCGTAGGGTTCATCGTATTAAGCTTAAATCTTCACCCCCTACGTCAGCCAGTCAAGGTCCCTTCTTCTCCATT<br>CTTTTCATTCTACGTTGTTTTCAAATCTATGAATCTTCTGGGTCTGTGCTTTTCTTATCGCTTCTATTCTATTCTATCCGTCATTTCTATTCAGTCGATTAATTCATTTTAGATCTGATTTAATATTAAACTATAG<br>ATCTGTTCTTGATTCCTGTTTCATGCTGTCGAAATCTGAAATCTGATTATATTGTCTATACCGTGGAGAATCACCATATTATTGTCTGCGAATACAAAGTGTTTGACTTTCAAT<br>CGTTTTTAATTATATATAAGTAAGACATATAAGTACCCATTATGTTGAAATCTTGATGGGTTCGTGGAGTTGAAAAATCACCATAGCAGTCTCACGTCCTGGTTTTAGAAATATCCTATTCAAAATTATATATTGTTTACTGTTTTAGATC<br>TGGACCTGAGACATATAAGTACCCATTATTGTTGAAACTTATGTCTCGGGTAAAATTTGCAAATTAATTGATTTCAAGATAACAATCAGAATCTTGATTCGTAGTTACGTAATACATGAAAA<br>AGTTTCATTTGGCTATGCTCACTCAGCTCATGTTATTTCTTGCAAATTAATTGATTAGTGTTATTTCATGAATGAGTTGCTTATCTCAACTGTTTCATTTTTTTGTCAAGTTGCTATTCTTAGAGACATTGTGA<br>ACAGTAAAAGATTGTATTTTGTTCTTCTTAAACGTGTTAGTCTATATGTGCAATAGAAGTCTATATGTTGAGAATTGATTCTCAACCTGTTCATTCATTTAGCTTCTTTTTTGTCAAGTTGCTATTCTTAGAGACATTGTGA<br>TTATGACTTGTCTTCTTAACCTAGTTTAGTTGCCACTTCTGCTTGCTGTTTTGCCACGTACTATCCATTTCTGTAACTATTAACGTAACTCTGAACCTGAACCTTGAACCTTTGTCTG<br>ATTTATTTTCTTTTCGTTGGTTTGGTTTAATTAACTTTTAAGTCTTGTTAAGTCTTGGAGAACTCAAGAAAACATGGGTGCAGGTGGAAGAATGCAAGTGTCCCCTCCTCCAAGAAGTCTGAAACCGACACCATCAAGGCGGTA<br>CCCTGGCAGACACCGCCCTGTTACTGTCCGGAGAACTCAAGAAGCAATCCCACCGGACTGTTTCTCCGCTCATCGGGACATCATCGGGACATCATAGCCTCCTGCTTCTACTA<br>CGTCGCCACCACTACCACCGGCTTGTTTGACGACAACCACCCTGCCGTCTCATCTTCCCACTGGCGTCTGGTCATAGCCACGAGTCGCGCCACCACGCCT<br>TCAGCGACTACCAGTCGTTTGACGACAACATCAGACATCAGAAGAGTCAGACAAAAGTCGTACGGCAAGTACCTCAACAAATCGCTCGTGTAGCCGTGCCGTTCACTTCTGCTTCACTCGCCGTTGTACTTAGCCTTCAACGTCTC<br>GTCGTTGTCCCGGAAGAAGTCAGACATCAGAAGAAGTCGGCTTCGGCTACGGCAAGTGGTACGGCAAGTTAACGGTGTTAACGGCGATCCTGCCGTTCGTTGCAGATCCAGGATTGTCTACGGTCAGATCTGTTCCGTT<br>GGGAAGACCCTTACGACGGCGGGGAGTGGCCTCGAGGGGAGCTTGGCTACCGTTGACACGGTGACAGAGACTACGGAATCTTGAACAAGTCTTCAACACAAGGGAATTGTTCAGTTCGATGGGACGCCGGTGGTTGGTGTTAAGGGCGATGTGAACCGGACGGAGCAAGGTGAGA<br>GAGTGGGCATTGGTTGAGGGGAGCTTTGGCTACCGTTGACACGGTGACAGAGACTATGATGATGAGGATTATGAGGATTAT GAGGATATTATGAGGATATTATGAGGATTAT GAGGATATTATGAGCTTATCTGTCTCCGATGCCGATTATCACGC<br>GATGGAAGCTACCAAGGCCGATACAACATTAAGTTATGCGATAATAAGTTATGAGGATATTATGAGGATATTATGAGGATATTATGAGGATTAT CAGTTCGATGGGACGCCGGTGTGTTAAGGCGATGTGTGAACCGGACGGAGCAAGGTGAGA<br>AGAAAGTGTGTTCTGGTACAACAATAAGTTATGAGGATATTATGAGGATATTATGACACATTTGACACATTTGACATTTGCTGTTTTCTGCAAGTTAGTGAAGTTAGGTGTCTAAAAATCTTGTCTGTATTGTTCTTCTTCTCATCGCTGTTATGTTGGGAT<br>CGTTGAAATGTGACTTTCGGACTAGTGAACCTTGGTTCTCGAACT |

Fig. 1

FAD-2 MUTANTS AND HIGH OLEIC PLANTS

FIELD OF THE INVENTION

The present invention relates to plants, seeds and products derived thereof, in particular to *Brassica* plants, seeds products derived thereof, that have mutant sequences conferring high oleic acid profile to the seed oil.

More particularly, the invention relates to mutant delta-12 fatty acid desaturase sequences, also referred to herein as FAD2 sequences, in such plants which confer high oleic acid profile on the seed oil.

BACKGROUND

Delta-12 fatty acid desaturase (also known as oleic desaturase or oleate desaturase) is involved in the enzymatic conversion of oleic acid to linoleic acid.

Varieties with high level of oleic acid (possibly combined with low level of linolenic acid) are sought for many different applications (food applications, health applications, biodiesel applications and many others).

Mutant seeds providing an oil exhibiting a high oleic acid content (oleic acid content higher that 70 wt. % based upon the total weight of fatty acids present in the oil) previously reported in the literature had very poor agronomic value and/or bad root characteristics, and/or very low yield capacity.

There is still a need for material having stable, high oleic acid content (possibly combined with stable low linolenic acid content) across locations and across years, with also good agronomic performances and with normal oilseed rape morphology. In particular, the plants should have no fasciation and should have normal root development.

SUMMARY OF THE INVENTION

The present invention relates to a nucleic acid molecule comprising (or consisting of) a nucleic acid sequence encoding a delta-12 oleate desaturase (FAD2) protein, said FAD2 protein having an amino acid substitution at position 108 relative to a wild-type FAD2 protein.

Another object is a nucleic acid molecule comprising (or consisting of) a nucleic acid sequence encoding a FAD2 protein, said FAD2 protein having an amino acid substitution at position 118 relative to a wild-type FAD2 protein.

Another object is a nucleic acid molecule comprising (or consisting of) a nucleic acid sequence encoding a FAD2 protein, said FAD2 protein having an amino acid substitution at position 108 and at position 118 relative to a wild-type FAD2 protein.

Preferably, said FAD2 protein is a *Brassica* FAD2 protein, more particularly a *Brassica napus* FAD2 protein.

Preferably, said substituted amino acid at position 108 is an Aspartic acid (replacing a Glycine in a wild-type FAD2 protein).

Preferably, said substituted amino acid at position 118 is a phenylalanine (replacing a Leucine in a wild-type FAD2 protein).

A preferred nucleic acid molecule of the invention comprises (or consists of) a nucleic acid of SEQ ID NO 1, 5, 11 or 12, its complementary form or its RNA form.

A nucleic acid molecule of the invention can comprise or consist of a nucleotide sequence having at least 80%, preferably at least 85%, more preferably at least 90% and even more preferably at least 95%, 96%, 97%, 98% or 99% identity with SEQ ID NO 1 or 11, or with the complementary form or RNA form thereof, encoding a FAD2 protein having an amino acid substitution at position 108 relative to a wild-type FAD2 protein.

A nucleic acid molecule of the invention can comprise or consist of a nucleotide sequence having at least 80%, preferably at least 85%, more preferably at least 90% and even more preferably at least 95%, 96%, 97%, 98% or 99% identity with SEQ ID NO 5 or 12, or with the complementary form or RNA form thereof, encoding a FAD2 protein having an amino acid substitution at position 118 relative to a wild-type FAD2 protein.

More particularly, said wild-type FAD2 protein comprises (or consists of) an amino acid sequence of SEQ ID NO 4 or 8.

Also object of the present invention is a fragment of at least 10, 15, 20, 25, 30, 40, 50, 100 or more nucleotides of a nucleic acid molecule according to the invention, said fragment comprising the mutated codon corresponding to said amino acid substitution at position 108, and/or the mutated codon corresponding to said amino acid substitution at position 118.

Said fragments can be used as primers, probes and/or selectable markers.

Any of the nucleic acid molecules of the invention can be used in a method of marker assisted selection of plants, preferably of *Brassica* species, more preferably of *Brassica napus* varieties, also object of the present invention.

Another object of the present invention is an assay kit which can comprise a first container containing any of the nucleic acid molecules of the invention.

Another object of the present invention is a FAD2 protein having an amino acid substitution at position 108, or corresponding to position 108, relative to a wild-type FAD2 protein such as the wild-type FAD2 protein represented by the amino acid sequence of SEQ ID NO 4 or 8.

Another object of the present invention is a FAD2 protein having an amino acid substitution at position 118, or corresponding to position 118, relative to a wild-type FAD2 protein such as the wild-type FAD2 protein represented by the amino acid sequence of SEQ ID NO 4 or 8.

Another object of the present invention is a FAD2 protein having an amino acid substitution at position 108, or corresponding to position 108, and an amino acid substitution at position 118, or corresponding to position 118 relative to a wild-type FAD2 protein such as represented by the amino acid sequence of SEQ ID NO 4 or B.

A preferred FAD2 protein of the invention comprises (or consists of) an amino acid sequence of SEQ ID No 2 or 6.

Another object of the present invention is a vector comprising a nucleic acid molecule encoding a mutant FAD2 protein according to the invention.

Another object of the present invention is a host cell comprising a vector of the invention and/or a nucleic acid sequence encoding a mutant FAD2 protein according to the invention.

Another object of the present invention is a plant stably transformed with a vector of the invention.

A plant to be transformed can be selected from the group consisting of oil producing crops, more particularly, from sunflowers, soybeans, cottons, corns and/or rapeseeds.

Another object of the present invention is a plant or a plant part or a seed containing a nucleotide sequence encoding a FAD-2 protein having an amino acid substitution at or corresponding to position 108 relative to a wild-type FAD-2 protein.

More particularly, a plant or a plant part or a seed according to the invention contains (or expresses) a FAD-2 protein having an amino acid substitution at or corresponding to position 108 relative to a wild-type FAD-2 protein.

Another object of the present invention is a plant or a plant part or a seed containing a nucleotide sequence encoding a PAD-2 protein having an amino acid substitution at or corresponding to position 118 relative to a wild-type PAD-2 protein.

More particularly, a plant or a plant part or a seed according to the invention contains (or expresses) a FAD-2 protein having an amino acid substitution at or corresponding to position 118 relative to a wild-type FAD-2 protein.

Another object of the present invention is a plant or a plant part or a seed containing a nucleotide sequence encoding a FAD-2 protein having an amino acid substitution at or corresponding to position 108 and an amino acid substitution at or corresponding to position 118 relative to a wild-type FAD-2 protein.

More particularly, a plant or a plant part or a seed according to the invention contains (or expresses) a FAD-2 protein having an amino acid substitution at or corresponding to 108 and an amino acid substitution at or corresponding to position 118 relative to a wild-type FAD-2 protein.

Another object of the present invention is a plant or a plant part or a seed containing a first nucleotide sequence encoding a FAD-2 protein having an amino acid substitution at or corresponding to position 108 and a second nucleotide sequence encoding a FAD-2 protein having an amino acid substitution at or corresponding to position 118 relative to a wild-type FAD-2 protein.

More particularly, a plant or a plant part or a seed according to the invention contains (or expresses) two FAD-2 proteins, one having an amino acid substitution at or corresponding to 108 and the other having an amino acid substitution at or corresponding to position 118 relative to a wild-type FAD-2 protein.

Preferably, said substituted amino acid at or corresponding to position 108 is aspartic acid (replacing a Glycine in a wild-type FAD2 protein).

Preferably, said substituted amino acid at or corresponding to position 118 is phenylalanine (replacing a Leucine in a wild-type FAD2 protein).

A plant or a plant part or a seed according to the invention can be obtained by a mutagenesis treatment, more particularly by an EMS treatment.

Progenies derived from said plant or plant part or seed are also objects of the invention.

Another object of the present invention is a vegetable oil obtained from seeds of the invention, said oil comprising more than (about) 72%, 75%, 80%, or 85%, of oleic acid based upon the total weight of the fatty acids present in the rapeseed oil.

Preferably, said oil further comprises less than (about) 4%, 3.5%, 3%, 2%, 1% or 0.5% of linolenic acid.

The invention also relates to food or feed products containing and/or prepared with a plant, a plant part, a seed and/or a vegetable oil according to the invention.

A method of enhancing the oleic acid content in a plant can comprise the step of transforming a plant with a vector of the invention.

Alternatively, a method of producing high oleic plant lines can comprise:
(a) crossing a first plant of the invention with a second plant,
(b) obtaining seeds from the cross of step (a)
(c) growing fertile plants from such seeds,
(d) obtaining progeny seeds from the plants of step (c), and
(e) identifying those seeds among the progeny that have high oleic acid content.

Alternatively, a method of producing high oleic plant lines can comprise:
(a) inducing mutagenesis in at least some cells from a plant, more particularly of a *Brassica* plant, and preferably of a *Brassica napus* variety that has a oleic acid content of less than 70%;
(b) regenerating plants from at least one of said mutagenized cells;
(c) selecting regenerated plants which have any of the nucleic acid sequences of the invention and/or which expresses a FAD2 protein according to the invention; and
(d) deriving further generations of plants from said regenerated plants.

BRIEF DESCRIPTION OF THE FIGURE

FIG. 1 corresponds to the list of sequences of the present invention.

DETAILED DESCRIPTION OF THE INVENTION

The present invention relates to plants, more particularly to *Brassica* plants, preferably to *Brassica napus* varieties, which have been created for providing an oil having an oleic acid content higher than 70 wt. %, based upon the total weight of fatty acids present in the oil.

More particularly, a plant of the invention has at least one mutated FAD2 gene of the invention.

Preferably, said mutated FAD2 gene confers high oleic acid content (i.e. a oleic acid content higher than 70 wt. %, based upon the total weight of fatty acids present in the oil) in seeds of said plants and in oil extracted from said seeds.

The present invention relates also to any part or any product of said plant bearing said at least one mutated FAD2 gene.

In the context of the present invention, a part or product of a plant is meant to encompass a leaf, cotyledon, stem, petiole, stalk, seed or any other tissue or fragment of tissue of said plant.

The present invention relates also to any progeny of said plant bearing said at least one mutated FAD2 gene of the invention.

In the context of the present invention, the term "progeny" refers to direct and indirect descendants, offspring and derivatives of a plant or plants of the invention and includes the first, second, third and/or subsequent generations, which may be produced by self crossing, crossing with plants with the same or different genotypes, and may be modified by range of suitable genetic engineering techniques.

The present invention also relates to said mutated FAD2 genes that confer high oleic acid content in seeds when present in a plant.

In particular, the invention relates to novel isolated nucleic acid molecules that encode novel variant forms of FAD2 protein having a substituted amino acid at position 108 (or corresponding to position 108) and/or a substituted amino acid at position 118 (or corresponding to position 118) relative to a wild-type FAD2 protein, such as the wild-type FAD2 protein represented by SEQ ID NO 4 and/or SEQ ID NO 8.

An isolated nucleic acid molecule of the invention contains at least one mutation, resulting in a substitution, preferably a substitution of aspartic acid for glycine, at (or corresponding to) position 108 and/or resulting in a substitution, preferably a substitution of phenylalanine for leucine, at (or corresponding to) position 118 relative to a wild-type FAD2 protein, such as the wild-type FAD2 protein represented by SEQ ID NO 4 and/or SEQ ID NO 8.

Said mutation(s) alter(s) the functionality of the resulting FAD2 gene product, whereby the level of oleic acid is modified, preferably increased, in plant expressing the mutant sequence(s), compared to the corresponding level in plant expressing the wild-type sequence(s).

In the framework of the present invention, except if otherwise specified, the term "at position 108" is to be understood as designating the amino acid position 108 in a wild-type FAD2 protein represented by SEQ ID NO 4 and/or SEQ ID NO 8, but also as referring to the amino acid corresponding to said position in a wild-type FAD2 protein that would have a different amino acid sequence due to deletions or additional amino acids in the polypeptide.

Similarly, the term "at position 118" is to be understood as designating the amino acid position 118 in a wild-type FAD2 protein represented by SEQ ID NO 4 and/or SEQ ID NO 8, but also as referring to the amino acid corresponding to said position in a wild-type FAD2 protein that would have a different amino acid sequence due to deletions or additional amino acids in the polypeptide.

The term "corresponding to position" as used herein means that a position is not only determined by the number of the preceding amino acids. The position of a given amino acid in accordance with the present invention may vary due to deletions or additional amino acids in the polypeptide. Thus, under a "corresponding position" in accordance with the present invention it is to be understood that the amino acid(s) referred to may differ in the indicated number but still has (have) similar neighbouring amino acids in the linear sequence.

In one aspect, a nucleic acid molecule of the invention encodes a FAD2D protein wherein the substitution for said amino acid corresponding to position 108 is a glutamate, and preferably is an aspartic acid.

More particularly, a nucleic acid molecule of the invention encodes a FAD2 protein having a substitution of an aspartic acid for a glycine at position 108 relative to a wild type FAD2 protein represented by the amino acid sequence of SEQ ID NO 4 or 8.

A nucleic acid molecule of the invention can comprise (or consist of) a nucleic acid sequence of SEQ ID NO 3, 5, 7, 9, 10 or 12, wherein the codon encoding the amino acid at position 108 has at least one mutation (or is mutated) to encode an amino acid different from glycine, and preferably to encode an aspartic acid at position 108 according to a FAD2 protein of the invention.

A preferred nucleic acid molecule of the invention comprises (or consists of) a nucleic acid sequence of SEQ ID NO 1 or 11.

In another aspect, a nucleic acid molecule of the invention encodes a FAD2 protein wherein the substitution for said amino acid corresponding to position 118 is a phenylalanine.

More particularly, a nucleic acid molecule of the invention encodes a FAD2 protein having a substitution of a phenylalanine for a leucine at position 118 relative to a wild type FAD2 protein represented by the amino acid sequence of SEQ ID NO 4 or 8.

A nucleic acid molecule of the invention can comprise (or consist of) a nucleic acid sequence of SEQ ID NO 1, 3, 7, 9, 10 or 11, wherein the codon encoding the amino acid at position 118 has at least one mutation (or is mutated) to encode an amino acid different from leucine, and preferably to encode a phenylalanine at position 118 according to a FAD2 protein of the invention.

A preferred nucleic acid molecule of the invention comprises (or consists of) a nucleic acid sequence of SEQ ID NO 5 or 12.

In another aspect, a nucleic acid molecule of the invention can encode a FAD2 protein having a deletion at position 118 relative to a wild type FAD2 protein, such as a wild type FAD2 protein represented by the amino acid sequence of SEQ ID NO 4 or 8.

More particularly, a nucleic acid molecule of the invention can encode a FAD2 protein having a leucine deleted at position 118 relative to a wild type FAD2 protein represented by the amino acid sequence of SEQ ID NO 4 or 8.

A nucleic acid molecule of the invention can comprise (or consist of) a nucleic acid sequence of SEQ ID NO 1, 3, 7, 9, 10 or 11, wherein the codon encoding the amino acid at position 118 has been deleted.

It will be appreciated by the skilled person that the nucleic acid sequences of SEQ ID NO 1 to 12 (i.e. SEQ ID NO 1, 3, 5, 7, 9, 10, 11 and 12) are not the only sequences that can be used to provide a FAD2 protein of the invention. Also contemplated are any nucleic acid molecules having different sequences but which, because of the degeneracy of the genetic code, encode a FAD2 protein comprising a substitution of an amino acid at position 108 (or corresponding to position 108) and/or a substitution of an amino acid at position 118 (or corresponding to position 118) relative to the wild-type amino acid sequence, such as the wild-type FAD2 protein represented by SEQ ID NO 4 or 8.

In particular, a nucleic acid molecule of the invention can comprise (or consist of) a nucleotide sequence having at least 80%, preferably at least 85%, more preferably at least 90% and even more preferably at least 95%, 96%, 97%, 98% or 99% identity with any of SEQ ID NO 1 to 12 (i.e. SEQ ID NO 1, 3, 5, 7, 9, 10, 11 and 12), or with the complementary form or RNA form thereof, encoding a FAD2 protein having an amino acid substitution at position 108 and/or 118 relative to a wild-type FAD2 protein, such as the wild-type FAD2 protein represented by SEQ ID NO 4 or 8.

More particularly, a nucleic acid molecule of the invention exhibits a nucleotide sequence having at least 80%, preferably at least 85%, more preferably at least 90% and even more preferably at least 95%, 96%, 97%, 98% or 99% identity with any of SEQ ID NO 1, 3, 5, 7, 9, 10, 11 and 12, or with the complementary form or RNA form thereof, and encodes a FAD2 protein having a substitution of an aspartic acid for a glycine at position 108 (or corresponding to position 108) and/or a substitution of a phenylalanine for a leucine at position 18 (or corresponding to position 118) relative to a wild type FAD2 protein represented by the amino acid sequence of SEQ ID NO 4 or 8.

A nucleic acid molecule of the invention can be derived from *Brassica napus* varieties, such as MSP05, MSP06, MSP07, MSP11 and/or 28DHS.059.

More particularly, a nucleic acid molecule of the invention has a mutation at position 1540 (also referred to as SNP1540) of the acid nucleic sequence of SEQ ID NO 11, which causes a change in genetic codon from GGC to GAC, resulting in a substitution of an amino acid at position 108 (or corresponding to position 108) relative to the wild-type amino acid sequence, such as the wild-type FAD2 protein represented by SEQ ID NO 4 or 8.

An isolated nucleic acid molecule of the invention containing said SNP1540 mutation, resulting in a substitution of aspartic acid for glycine at position 108, alters the functionality of the resulting FAD2 gene product, whereby the level of oleic acid is increased in plant expressing the mutant sequence, compared to the corresponding level in plant expressing the wild-type sequence.

In the framework of the invention, the term "SNP1540" refers to the single nucleotide polymorphism corresponding to said mutation at position 1540 of the nucleic acid of SEQ ID NO 11, and can refer also to the corresponding mutation in any nucleic acid molecule encoding a FAD2 protein of the invention having a substituted amino acid at position 108 (or corresponding to position 108) relative to the wild-type FAD2 protein, such as the wild-type FAD2 protein represented by SEQ ID NO 4 or 8.

Any fragment of a nucleic acid molecule of the invention of at least 10, 15, 20, 25, 50, 100 or more nucleotides comprising said SNP1540 is contemplated.

In another aspect, novel nucleic acid molecules are derived from *Brassica napus* varieties, such as MSP05, MSP11 and/or 28DHS.059 having a mutation (SNP1590) resulting in a substitution of an amino acid at position 118 of the FAD2 wild-type sequence, such as represented by SEQ ID NO 8.

More particularly, a nucleic acid molecule of the invention has a mutation at position 1590 (also referred to as SNP1590) of the acid nucleic sequence of SEQ ID NO 12, which causes a change in genetic codon from CTT to TTT, resulting in a substitution of an amino acid at position 118 (or corresponding to position 118) relative to the wild-type amino acid sequence, such as the wild-type FAD2 protein represented by SEQ ID NO 4 or 8.

An isolated nucleic acid molecule of the invention containing said SNP1590 mutation, resulting in a substitution of phenylalanine for leucine at position 118, alters the functionality of the resulting FAD2 gene product, whereby the level of oleic acid is increased in plant expressing the mutant sequence, compared to the corresponding level in plant expressing the wild-type sequence.

In the framework of the invention, the term "SNP1590" refers to the single nucleotide polymorphism corresponding to said mutation at position 1590 of the nucleic acid of SEQ ID NO 12, and can refer also to the corresponding mutation in any nucleic acid molecule encoding a FAD2 protein of the invention having a substituted amino acid at position 118 (or corresponding to position 118) relative to the wild-type FAD2 protein, such as the wild-type FAD2 protein represented by SEQ ID NO 4 or 8.

Any fragment of a nucleic acid molecule of the invention of at least 10, 15, 20, 25, 50, 100 or more nucleotides comprising said SNP1590 is contemplated.

Also contemplated is any fragment of a nucleic acid molecule of the invention of at least 10, 15, 20, 25, 50, 100 or more nucleotides comprising said SNP1540 and said SNP1590.

Any fragment of a nucleic acid molecule of the invention of at least 10, 15, 20, 25, 50, 100 or more nucleotides and comprising at least one mutation resulting in a FAD2 protein according to the invention is contemplated.

In other words, also contemplated is any fragment of a nucleic acid molecule of the invention of at least 10, 15, 20, 25, 30, 40, 50, 100, 500 or more nucleotides and comprising at least one mutation in the codon encoding said amino acid at position 108 (or corresponding to position 1.08), and/or in the codon encoding said amino acid at position 118 (or corresponding to position 118) relative to the wild-type FAD2 protein, such as the wild-type FAD2 protein represented by SEQ ID NO 4 or 8.

Such fragments can be used as primers, as probes and/or as markers.

The nucleic acid fragments of the invention can be used as markers in plant genetic mapping and plant breeding programs.

Such markers may include restriction fragment length polymorphism (RFLP), random amplification polymorphism detection (RAPD), polymerase chain reaction (PCR) or self-sustained sequence replication (3SR) markers, for example.

Marker-assisted breeding techniques may be used to identify and follow a plant according to the invention or its progeny, also object of the invention, during the breeding process.

Marker-assisted breeding techniques may be used in addition to, or as an alternative to, other sorts of identification techniques.

An example of marker-assisted breeding is the use of PCR primers that specifically amplify a nucleic acid molecule of the invention.

The invention thereby provides methods for segregation and selection analysis of genetic crosses involving plants having nucleic acid sequences of the invention.

A method of the invention may for example involve determining the presence in a genome of particular FAD2 alleles containing at least one mutation resulting in a substitution (preferably a substitution of aspartic acid for glycine) at (or corresponding to) position 108 and/or resulting in a substitution (preferably a substitution of phenylalanine for leucine) at (or corresponding to) position 118 relative to a wild type FAD2 protein, such as the wild type FADS protein represented by SEQ ID NO 4 or B.

Such a determination may for example be achieved with a range of techniques, such as PCR amplification, DNA fingerprinting, RNA fingerprinting, gel blotting and RFLP analysis, nuclease protection assays, sequencing of the relevant nucleic acid fragment, the generation of antibodies (monoclonal or polyclonal), or alternative methods adapted to distinguish the protein produced by the relevant alleles from other variant forms of that protein or from the wild-type.

More particularly, such fragments can be used in method of marker assisted selection for high oleic traits in plants, preferably in *Brassica* species, more particularly in *Brassica napus* varieties.

Another aspect of the present invention is related to a recombinant nucleotide sequence comprising, operably linked to a nucleotide sequence according to the invention, one or more adjacent regulatory sequence(s). Said adjacent regulatory sequence(s) is/are preferably originating from homologous organisms.

However said adjacent regulatory sequences may also be originating from heterologous organisms.

Said adjacent regulatory sequences are specific sequences such as promoters, enhancers, secretion signal sequences and/or terminators.

Another aspect of the invention is related to a vector comprising a nucleic acid molecule of the invention, possibly operably linked to one or more adjacent regulatory sequencers) originating from homologous or from heterologous organisms.

In the present context "vector" is defined as any biochemical construct which may be used for the introduction of a nucleotide sequence (by transduction, transfection, transformation, infection, conjugation, etc.) into a cell.

Advantageously, a vector according to the invention is selected from the group consisting of plasmids (including replicative and integrative plasmids), viruses, phagemids, chromosomes, transposons, liposomes, cationic vesicles, or a mixture thereof. Said vector may already comprise one or more adjacent regulatory sequencers), allowing the expression of said nucleic acid molecule and its transcription into a polypeptide of the invention.

The invention also relates to a FAD2 polypeptide having an amino acid substitution at (or corresponding to) position 108 relative to a wild type FAD2 protein, such as a wild-type FAD2 protein represented by SEQ ID NO 4 or 8.

More particularly, a FAD2 polypeptide of the invention comprises (or consists of) the amino acid sequence of SEQ ID NO 6 further comprising a substitution of aspartic acid for glycine at position 108.

A preferred FAD2 polypeptide of the invention comprises (or consists of) the amino acid sequence of SEQ ID NO 2, The invention also relates to a FAD2 polypeptide having an amino acid substitution at (or corresponding to) position 118 relative to a wild type FAD2 protein, such as a wild-type FAD2 protein represented by SEQ ID NO 4 or 8.

More particularly, a FAD2 polypeptide of the invention comprises (or consists of) the amino acid sequence of SEQ ID NO 2 further comprising a substitution of phenylalanine for leucine at position 118.

A preferred FAD2 polypeptide of the invention comprises (or consists of) the amino acid sequence of SEQ ID NO 6.

The present invention also encompasses any fragments of a FAD2 protein of the invention having a delta-12 oleate desaturase activity and comprising said substitution(s) at position 108 and/or 118.

Nucleic acid molecules, recombinant nucleic acid molecules, and/or vectors of the present invention are useful to transform target plants, and thereby confer altered FAD2 gene product, whereby the level of oleic acid is modified, preferably increased, in plant expressing a mutant FAD2 of the invention, compared to the corresponding level in plant expressing the wild-type sequence.

The present invention is also related to a transformed host cell, or recombinant host cell, containing (or having incorporated) one or more of the nucleotide sequences and/or vectors according to the invention.

In the present context, a "transformed host cell" or "recombinant cell", also referred to as "transformant", is a cell having incorporated one or more of the nucleotide sequences and/or vectors according to the invention. The transformed host cell may be a cell in which said vector(s) and/or said nucleotide sequencers) is/are introduced by means of genetic transformation, preferably by means of homologous recombination, or by any other well known methods used for obtaining a recombinant organism.

Any method by which the novel sequence can be incorporated into the host genome is contemplated by the present invention.

More particularly, any method by which the novel sequence can be incorporated into the host genome, and stably inherited by its progeny, is contemplated by the present invention.

A broad range of known techniques currently exist for achieving direct or indirect transformation of higher plants with exogenous DNA.

Transformation of plant cells can be mediated by the use of vectors. A common method of achieving transformation is the use of *Agrobacterium tumefaciens* to introduce a foreign gene into the target plant cell.

Plant viruses also provide a possible means for transfer of exogenous DNA.

Direct uptake of plant cells can also be employed. Typically, protoplasts of the target plant are placed in culture in the presence of the nucleic acid molecules to be transferred, and an agent which promotes the uptake of said nucleic acid molecules by protoplast. Useful agents in this regard are polyethylene glycol or calcium phosphate.

Alternatively, nucleic acid molecules uptake can be stimulated by electroporation. In this method, an electrical pulse is used to open temporary pores in a protoplast cell membrane, and said nucleic acid molecules in the surrounding solution are then drawn into the cell through the pores. Similarly, microinjection can be employed to deliver said nucleic acid molecules directly into a cell, and preferably directly into the nucleus of the cell.

In these techniques, transformation occurs in a plant cell in culture. Subsequent to the transformation event, plant cells can be regenerated to whole plants.

Techniques for the regeneration of mature plants from callus or protoplast culture are well known.

Alternate methods are also available which do not necessarily require the use of isolated cells, and therefore, plant regeneration techniques, to achieve transformation. These are generally referred to as "ballistic" or "particle acceleration" methods, in which nucleic acid molecules coated metal particles are propelled into plant cells by either a gunpowder charge or electrical discharge. In this manner, plant cells in culture or plant reproductive organs or cells, e.g. pollen, can be stably transformed with the nucleic acid molecules of interest.

The present invention can be applied to transformation of virtually any type of plant, monocotyledons or dicotyledons.

Suitable plants to be transformed are preferably oil producing crops, such as sunflower, soybean, cotton, corn, etc., preferably *Brassica* species, more preferably *Brassica napus* varieties.

In one aspect of the invention, a plant comprises at least one FAD2 coding sequence of the invention.

A plant of the invention can comprise a nucleic acid sequence of SEQ ID NO 5 or a nucleic acid sequence of SEQ ID NO 12.

Preferably, a plant of the invention comprises a nucleic acid sequence of SEQ ID NO 11 or a nucleic acid sequence of SEQ ID NO 1, such as MSP06 or MSP07.

In another aspect of the invention, a plant comprises two FAD2 coding sequences of the invention.

In particular, a plant of the invention comprises a nucleic acid sequence of SEQ ID NO 11 and a nucleic acid sequence of SEQ ID NO 12, such as MSP05, MSP11 or 28DHS.059.

Preferably, a plant of the invention comprises a nucleic acid sequence of SEQ ID NO 1 and a nucleic acid sequence of SEQ ID NO 5, such as MSP05, MSP11 or 28DHS.059.

MSP06 variety is maintained as a Budapest Treaty patent deposit with NCIMB, Bucksburn, Aberdeen, AB21 9YA, Scotland, under accession number NCIMB 41367 made Dec. 22, 2005.

MSP07 variety is maintained as a Budapest Treaty patent deposit with NCIMB, Bucksburn, Aberdeen, AB21 9YA, Scotland, under accession number NCIMB 41368 made Dec. 22, 2005.

28DHS.059 variety is maintained as a Budapest Treaty patent deposit with NCIMB, Bucksburn, Aberdeen, AB21 9YA, Scotland, under accession number NCIMB 41364 made Dec. 22, 2005.

MSP05 variety is maintained as a Budapest Treaty patent deposit with NCIMB, 23 St. Machar Drive, Aberdeen, AB24 3RY, Scotland, under accession number NCIMB 41233 made Jul. 9, 2004.

MSP11 variety is maintained as a Budapest Treaty patent deposit with NCIMB, 23 St. Machar Drive, Aberdeen, AB24 3RY, Scotland, under accession number NCIMB 41234 made Jul. 9, 2004.

Another object of the invention is a method of producing high oleic plant lines comprising: (a) crossing a first plant with a second plant having at least one mutant FAD2 gene according to the invention, (b) obtaining seeds from the cross of step (a), (c) growing fertile plants from such seeds; (d)

obtaining progeny seeds from the plants of step (c), and (e) identifying those seeds among the progeny that have high oleic acid content.

In another aspect, the invention provides a method for increasing the oleic acid content of plants, more particularly of *Brassica* plants, and preferably of *Brassica napus* plants comprising the steps of:

(a) inducing mutagenesis in at least some cells from a plant, more particularly of a *Brassica* plant, and preferably of a *Brassica napus* plant that has a oleic acid content of less than 70%;
(b) regenerating plants from at least one of said mutagenized cells;
(c) selecting regenerated plants which have a nucleic acid sequence of the invention and/or which expresses a FAD2 protein of the invention; and
(d) deriving further generations of plants from said regenerated plants.

Preferably, the seeds obtained from said plants provide an oil having an oleic acid content of more than 70 wt. %, more preferably of more than 75 wt. %, based upon the total weight of fatty acid present the oil.

Another object of the invention is a vegetable oil obtained from at least one plant according to the invention, which vegetable oil comprises more than (about) 70%, 72%, 75%, 80%, or 85% of oleic acid.

More particularly, a vegetable oil of the invention, obtained preferably from at least one *Brassica* species of the invention, more preferably from at least one *Brassica napus* variety according to the invention, comprises more than (about) 70%, 72%, 75%, 80%, or 85% of oleic acid. Said oil can further comprise less than (about) 4%, 3.5%, 3%, 2%, 1% or 0.5% of linolenic acid, based upon the total weight of the fatty acids present in the oil.

Preferably, said oil comprises more than (about) 70%, 72%, 75%, 80%, 81%, 82%, 83%, 84%, 85%, 86%, 87%, 88%, 89% or 90%, preferably between (about) 70% and (about) 90%, more preferably between (about) 72% and (about) 89% of oleic acid. Said oil can further comprise less than (about) 4%, 3.5%, 3%, 2%, 1%, or 0.5%, preferably between (about) 4% and (about) 0.4% of linolenic acid, based upon the total weight of the fatty acids present in the oil.

According to a preferred embodiment, two double low winter rapeseed varieties (ENVOL and LIBERATOR) were submitted to an Ethyl Methane Sulfonate (EMS) treatment in 1992. The EMS treatment was performed at 2.5% and 5% for 4 h or 8 h.

The M1 generation was grown in a greenhouse after 8 weeks of vernalization in a growth chamber and then harvested in July 93.

M1 seeds were planted in the field in September 93, bagged at the beginning of flowering and M2 seeds harvested in July 94.

M2 seeds were planted in September 94, bagged at the beginning of flowering and M3 seeds harvested in July 95.

The progenies were then analysed for fatty acid composition using gas chromatography based analytical method, as commonly known in this area of technology.

All progenies showing an oleic content higher than 68% were kept.

Selected progeny was replanted in the field in September 1995, bagged in April then harvested in July 1996.

At this stage progenies were screened for good agronomic and morphological characteristics, such as good germination capacity, good autumn vigor, good winter hardiness, good rooting system, good blackleg and light leaf spot resistance as well as excellent lodging resistance.

Material which was too tall and too late was eliminated as well as material showing strong fasciation.

Analysis of the remaining progeny was again done by gas chromatography to select individuals with oleic acid levels higher than 68%. All of these individuals were planted in the field in September 1996-1997.

A progeny called MUT 152-96 looked particularly interesting in terms of agronomic and morphological characteristics, as well as for its oleic acid content. It was cultivated in isolation during the crop season of September 1996-1997. The most interesting progenies in terms of agronomic and morphological characteristics were selected for bagging and crossing.

Crossing was performed with double low winter oilseed rape varieties having a conventional fatty acid profile (i.e. oleic acid below 70%) or with low linolenic acid content (i.e. less than about 3.5%) in order to develop lines with a high oleic acid content associated with low linolenic acid content (HOLL).

The material was progressed into pedigree breeding, self pollination until at least the F7 generation.

At all generations strong selection pressure was applied against fasciation and for normal plant development and normal rooting system.

Fatty acid composition was monitored in each generation and only material with oleic acid content higher than 75% and linolenic acid content below 3.5% was kept.

The following HOLL varieties were obtained by this process: MSP05, MSP06, MSP07, MSP11, 28 DHS 059.

The double low varieties with conventional fatty acid profiles used in this work were BRISTOL, CAPITOL, CAPVERT, VIVOL and CAIMAN and these have been multiplied or maintained using the same maintenance scheme as described here above for the HOLL lines.

Basic seed was used for the determination of fatty acid content in trials—small research trials (6 to 12 m$^2$) or development trials (500 m$^2$) and for the sequencing work.

EXAMPLES

Example 1

The seeds were grinded in a first solution consisting of methanol (800 ml), trimethyl-pentane (200 ml) and 5 g of Na OH. About 3 ml of solution was used for about 10 g of seeds (in other words about 10 to 50 seeds for 1 ml of solution).

Extraction was performed during 20 minutes and thereafter a second solution, consisting of trimethylamine (900 ml) and propanol, 2-(100 ml), was added at the same volume as the first solution.

The resulting solution was vortexed and allowed to rest until formation of an upper phase.

The upper phase was sampled and transferred into viols.

One microliter of same was injected in a gas chromatograph (Fisons from thermo-electron with a column DB3-30 meter with a diameter of 0.25 mm and a thickness of 25 micrometer). Running time was about 4 min.

The oleic acid content results are summarized in table 1.

TABLE 1

| Varieties | Oleic acid content (wt. %) | Appreciation |
|---|---|---|
| MSP05 | 78.1-81.9 | Very high |
| MSP06 | 75.6-78.5 | High |
| MSP07 | 76.7-79.4 | High |
| MSP11 | 80.2-83.9 | Very high |

TABLE 1-continued

| Varieties | Oleic acid content (wt. %) | Appreciation |
|---|---|---|
| 28DHS059 | 83.8-84.9 | Very high |
| BRISTOL | 61.4-65.7 | Normal |
| VIVOL | 60.8-63.2 | Normal |
| CAPVERT | 58.9-65.9 | Normal |
| CAIMAN | 61.9-64.0 | Normal |
| CAPITOL | 59.7-64.6 | Normal |

The oleic acid content is based on the total weight of the fatty acid in the extracted oil.

Example 2

Plant materials used for sequencing are:
mutant lines with higher oleic fatty acid content: MSP05, MSP06, MSP07, MSP11 and 28DHS.059; and
wild type varieties with normal oleic acid content: Bristol, Capitol, Vivol, Capvert and Caiman.

All these lines were grown in a growth chamber and the cotyledons and stems were collected from 7-day-old plants.

The plant tissues were freeze-dried and used for DNA extraction.

DNA was isolated with Qiagen Plant DNA kits (Qiagen INC-USA, Valencia Calif.).

PCR was performed with TaqGold protocol (AB Biosystem, Inc,).

Reaction mix includes 2.5 µl 10× buffer, 0.2 µl TaqGold, 0.2 µl dNTP (25 mM), 2 µl primers (5 uM) and 10 ul DNA template (2 ng/ul) and 10.1 ul H₂O.

PCR cycles were as follows: 94° C. 5 min; 8 cycles of 94° C. 40 sec, 62° C. 40 sec, 72° C. 1 min, 94° C. 40 sec, 60° C. 40 sec, 72° C. 1 min, 94° C. 40 sec, 58° C. 40 sec, 72° C. 1 min, 94° C. 40 sec, 56° C. 40 sec, 72° C. 1 min, 3 cycles of 94° C. 40 sec, 55° C. 40 sec, 72° C. 1 min; hold at 72° C. for 7 min.

PCR products were analyzed on 1% agarose gel.

For sequencing, 5 µl PCR products were removed to a new tube and 1 µl ExonucleaseI (1:50 dilution) and 1 µl Shrimp Alkaline Phosphatase (1.5 dilution).

The mix was incubated at 37° C. for 20 min and then 80° C. for 15 min to inactivate the enzymes.

40 µl H2O was added and 6 µl were used as template with 1 µl sequencing primer.

Sequencing was done on 3730 DNA Analyzer (Applied Biosystems).

Sequences were assembled and aligned using SeqMan II program of the LaserGene (DNASTAR, INC, Madison. WI).

Example 3

Four *Brassica napus* delta-12 oleate desaturase (FAD2) gene sequences, 4684997, 46399190, 8705228 and 4092878, were downloaded from Genebank (NCBI). These sequences were used as queries to blast against Monsanto sequence database.

Using the "blastn" programs (NCBI), a number of high score hits were obtained. All the hit sequences were downloaded and reassembled with the SeqmanII program (DNASTAR Inc, Madison, Wis., USA).

Two distinct transcripts were identified and designated as Fad2-1 (SEQ ID NO 9) and Fad2-2 (SEQ ID NO 10). Fad2-1 and Fad2-2 share a high sequence homology, with 97% sequence identity.

To identify causative mutations associated with high oleic acid content in the mutant lines and their progenies, nested locus-specific primers were designed to cover the entire sequences.

The 3' end of a primer was always located at a nucleotide that differentiated Fad2-1 from Fad2-2 except those located at 5' and 3' ends of the consensus sequences where there was not differential nucleotide between the two genes.

The primers were also designed in such way that one amplicon would overlap with another to ensure full coverage of the entire sequence. These primers were arrayed and used to generate locus-specific amplicons on mutants and wild types. Sequencing results indicated that all the locus-specific PCR primers behaved as expected.

Sequences belonging to the same gene were assembled together using SeqManII program.

The consensus genomic sequences of the mutated Fad2-1 and Fad2-2 genes are represented respectively by SEQ ID NO 11 and 12.

Table 2 summarizes the sequence features of both Fad2-1 and Fad2-2 genes.

TABLE 2

| Features | FAD2-1 position | FAD2-2 position |
|---|---|---|
| Gene | 1-2614 | 1-2666 |
| 5' UTR | 1-1217 | 1-1238 |
| Exon | 1-108 | 1-111 |
| Intron | 109-1213 | 112-1234 |
| Exon | 1214-2614 | 1235-2619 |
| CDS | 1218-2372 | 1239-2393 |
| 3' UTR | 2373-2614 | 2394-2666 |

The features are based on the consensus genomic sequences from multiple reads on different genotypes.

Both Fad2-1 and Fad2-2 genes have one intron each.

The intron sizes are slightly different between two genes. For Fad2-1 intron spans 1105 bp starting from position 109 to 1213, while for Fad2-2, intron consists of 1123 bp starting from position 112 to 1234 on the consensus sequences.

The intron is located at 5'UTR region.

Putative translation initiation codons are located at 1218 and 1239 for Fad2-1 and Fad2-2 genes, respectively.

The translation termination codons are located at 2370-2372 and 2391-2393, respectively for Fad2-1 and Fad2-2.

3'UTR sequences are 247 base pairs for Fad2-1 and 273 base pairs for Fad2-2 genes.

A transition mutation was found at position 1540 (called SNP1540) of FAD2-1 gene (as represented by SEQ ID NO 11), which caused a change in genetic codon from GGC to GAC, resulting in an alternation of amino acid residue from Glycine to Aspartic acid.

Since Glycine and Aspartic acid have very different properties in term of hydrophobicity, charges and polarity etc., the mutation causes a radical change in the enzyme function in mutant lines.

Also, highly conserved amino acid sequences between plant delta-12 fatty acid desaturases and plant delta-15 fatty acid desaturases have been reported (U.S. Pat. No. 6,872,872 B1). Among others, one conserved amino acid sequence motifs mentioned is AHECGH. The SNP1540 happened to locate on the same motif. The "G" in the motif was mutated to a "D". Because conserved regions usually implied a functional or structural significance, mutation at this conserved region has caused adverse effects on the FAD2-1 enzyme, resulting in high oleic acid content in mutant lines MSP11, MSP05, MSP06, MSP07 and 28DHS.059.

A point mutation at position 1590 (called SNP1590) of FAD2-2 gene (as represented by SEQ ID NO 12) caused an amino acid residue change from leucine (CTT) to phenylalanine (TTT).

Both leucine and phenylalanine are hydrophobic in nature and share some common amino acid properties, but phenylalanine contains a large rigid aromatic group on the side chain that causes some change in the function of the enzyme.

Moreover, in combination with SNP1540 mutation, this mutation causes more visible effect on the phenotype.

Combination of different alleles at these mutations created a gradient on oleic content as observed on different mutant lines (see table 1).

Three mutant lines, MSP11, MSP05 and 28DHS.059, carried double mutations at SNP1540 and SNP1590. Since both mutations were missense mutations, the FAD2 gene functions are severely affected, resulting in highest oleic content among the mutant lines.

Oleic content for MSP05 was lower than the other two mutants. This was because oleic content was obtained from only one-year data which could be subject to variations due to environmental effect.

Two mutant lines, MSP06 and MSP07, carried a single point mutation at SNP1540. Since they are less severe than the double mutants, oleic content for these two lines were slightly below the double mutants.

In summary, the sequence data strongly indicated that these mutations at Fad2-1 and Fad2-2 are highly associated with oleic contents on different mutant lines.

Combination of different alleles explains all the phenotypic variations of oleic content in the plant materials obtained.

The identification of causative sequence variations is crucial to design diagnostic assays specifically for each mutant allele.

Knowledge of association between sequence variations and phenotypes can allow to design marker assays to accurately predict the oleic acid content in plants without the need of wet chemical analysis of the fatty acid content.

---

The invention claimed is:

1. An isolated nucleic acid molecule comprising a nucleic acid sequence encoding a delta-12 oleate desaturase FAD2 protein, said FAD2 protein having an amino acid substitution at position 108, or at a position corresponding to position 108, relative to a wild-type FAD2 protein represented by SEQ ID NO. 4 or SEQ ID NO. 8.

2. The isolated nucleic acid molecule according to claim 1, wherein said FAD2 protein is a *Brassica* FAD2 protein.

3. The isolated nucleic acid molecule according to claim 1, wherein said amino acid at position 108 or at a position corresponding to position 108 is changed to an aspartic acid.

4. An isolated nucleic acid molecule comprising a nucleic acid of SEQ ID NO. 1, its complementary form or RNA form.

5. An isolated nucleic acid molecule comprising a nucleotide sequence having at least 80% identity with SEQ ID NO. 1, or with the complementary form or RNA form thereof, encoding a FAD2 protein having an amino acid substitution at position 108, or at a position corresponding to position 108, relative to a wild-type FAD2 protein represented by SEQ ID NO. 4 or SEQ ID NO. 8.

6. A fragment of at least 10 nucleotides of an isolated nucleic acid molecule according to claim 1, said fragment comprising the mutated codon corresponding to said amino acid substitution at position 108 or at a position corresponding to position 108.

7. A FAD2 protein having an amino acid substitution at position 108, or corresponding to position 108, relative to a wild-type FAD2 protein represented by the amino acid sequence of SEQ ID NO. 4 or 8.

8. A FAD2 protein comprising an amino acid sequence of SEQ ID NO. 2.

9. A vector comprising a nucleic acid molecule according to claim 1.

10. A vector comprising a nucleic acid molecule according to claim 3.

11. A host cell comprising a nucleic acid sequence according to claim 1.

12. A host cell comprising a vector according to claim 10.

13. A plant stably transformed with a vector of claim 9, said plant being selected from the group consisting of sunflower, soybean, cotton, corn and rapeseed.

14. A plant stably transformed with a vector of claim 10, said plant being selected from the group consisting of sunflower, soybean, cotton, corn and rapeseed.

15. A method of enhancing the oleic acid content in a plant comprising transforming a plant with the vector of claim 9.

16. A method of enhancing the oleic acid content in a plant comprising transforming a plant with the vector of claim 10.

17. A method of producing high oleic plant lines comprising:
    (a) crossing a first plant according to claim 13 with a second plant,
    (b) obtaining seeds from the cross of step (a),
    (c) growing fertile plants from such seeds,
    (d) obtaining progeny seeds from the plants of step (c), and
    (e) identifying those seeds among the progeny that have high oleic acid content.

18. A method of producing high oleic plant lines comprising:
    (a) crossing a first plant according to claim 14 with a second plant,
    (b) obtaining seeds from the cross of step (a),
    (c) growing fertile plants from such seeds,
    (d) obtaining progeny seeds from the plants of step (c), and
    (e) identifying those seeds among the progeny that have high oleic acid content.

19. A method of producing high oleic plant lines comprising:
    (a) inducing mutagenesis in at least some cells from a plant that has an oleic acid content of less than 70%;
    (b) regenerating plants from at least one of said mutagenized cells;
    (c) selecting regenerated plants which have a nucleic acid sequence according to claim 1; and
    (d) deriving further generations of plants from said regenerated plants.

20. The method according to claim 19, wherein the at least some cells from a plant are from a *Brassica* plant.

21. The method according to claim 20, wherein the *Brassica* plant is a *Brassica napus* plant.

22. The method of claim 21 wherein the selecting comprises selecting regenerated plants having a nucleic acid sequence according to claim 1 and further having a second nucleic acid sequence encoding a second delta-12 oleate desaturase FAD2 protein, said second FAD2 protein having an amino acid substitution at position 118, or at a position corresponding to position 118, relative to a wild-type FAD2 protein represented by SEQ ID NO. 4 or SEQ ID NO. 8.

23. A plant obtainable by the method of claim 22 comprising: a first nucleotide sequence encoding a first FAD2 protein, said first FAD2 protein having an amino acid substitution at position 108, or at a position corresponding to position 108, relative to a wild-type FAD2 protein; and a second nucleotide sequence encoding a second FAD2 protein, said second FAD2 protein having an amino acid substitution at position 118, or at a position corresponding to position 118, relative to a wild-type FAD2 protein represented by SEQ ID NO. 4 or SEQ ID NO. 8.

24. The isolated nucleic acid molecule according to claim 2, wherein the *Brassica* FAD2 protein is a *Brassica napus* FAD2 protein.

* * * * *

SEQUENCE LISTING

<160> NUMBER OF SEQ ID NOS: 12

<210> SEQ ID NO 1
<211> LENGTH: 1155
<212> TYPE: DNA
<213> ORGANISM: Brassica napus
<220> FEATURE:
<221> NAME/KEY: CDS
<222> LOCATION: (1)..(1155)

<400> SEQUENCE: 1

```
atg ggt gca ggt gga aga atg caa gtg tct cct ccc tcc aaa aag tct      48
Met Gly Ala Gly Gly Arg Met Gln Val Ser Pro Pro Ser Lys Lys Ser
1               5                   10                  15 gaa acc gac aac atc aag cgc gta ccc tgc gag aca ccg ccc ttc act      96
Glu Thr Asp Asn Ile Lys Arg Val Pro Cys Glu Thr Pro Pro Phe Thr
                20                  25                  30 gtc gga gaa ctc aag aaa gca atc cca ccg cac tgt ttc aaa cgc tcg     144
Val Gly Glu Leu Lys Lys Ala Ile Pro Pro His Cys Phe Lys Arg Ser
            35                  40                  45 atc cct cgc tct ttc tcc tac ctc atc tgg gac atc atc ata gcc tcc     192
Ile Pro Arg Ser Phe Ser Tyr Leu Ile Trp Asp Ile Ile Ile Ala Ser
        50                  55                  60 tgc ttc tac tac gtc gcc acc act tac ttc cct ctc ctc cct cac cct     240
Cys Phe Tyr Tyr Val Ala Thr Thr Tyr Phe Pro Leu Leu Pro His Pro
65                  70                  75                  80 ctc tcc tac ttc gcc tgg cct ctc tac tgg gcc tgc cag ggc tgc gtc     288
Leu Ser Tyr Phe Ala Trp Pro Leu Tyr Trp Ala Cys Gln Gly Cys Val
                85                  90                  95 cta acc ggc gtc tgg gtc ata gcc cac gag tgc gac cac cac gcc ttc     336
Leu Thr Gly Val Trp Val Ile Ala His Glu Cys Asp His His Ala Phe
            100                 105                 110 agc gac tac cag tgg ctg gac gac acc gtc ggc ctc atc ttc cac tcc     384
Ser Asp Tyr Gln Trp Leu Asp Asp Thr Val Gly Leu Ile Phe His Ser
        115                 120                 125 ttc ctc ctc gtc cct tac ttc tcc tgg aag tac agt cat cga cgc cac     432
Phe Leu Leu Val Pro Tyr Phe Ser Trp Lys Tyr Ser His Arg Arg His
    130                 135                 140 cat tcc aac act ggc tcc ctc gag aga gac gaa gtg ttt gtc ccc aag     480
His Ser Asn Thr Gly Ser Leu Glu Arg Asp Glu Val Phe Val Pro Lys
145                 150                 155                 160 aag aag tca gac atc aag tgg tac ggc aag tac ctc aac aac cct ttg     528
Lys Lys Ser Asp Ile Lys Trp Tyr Gly Lys Tyr Leu Asn Asn Pro Leu
```

-continued

```
                         165                 170                 175
gga cgc acc gtg atg tta acg gtt cag ttc act ctc ggc tgg cct ttg    576
Gly Arg Thr Val Met Leu Thr Val Gln Phe Thr Leu Gly Trp Pro Leu
            180                 185                 190 tac tta gcc ttc aac gtc tcg ggg aga cct tac gac ggc ggc ttc gct    624
Tyr Leu Ala Phe Asn Val Ser Gly Arg Pro Tyr Asp Gly Gly Phe Ala
                195                 200                 205 tgc cat ttc cac ccc aac gct ccc atc tac aac gac cgt gag cgt ctc    672
Cys His Phe His Pro Asn Ala Pro Ile Tyr Asn Asp Arg Glu Arg Leu
    210                 215                 220 cag ata tac atc tcc gac gct ggc atc ctc gcc gtc tgc tac ggt ctc    720
Gln Ile Tyr Ile Ser Asp Ala Gly Ile Leu Ala Val Cys Tyr Gly Leu
225                 230                 235                 240 tac cgc tac gct gct gtc caa gga gtt gcc tcg atg gtc tgc ttc tac    768
Tyr Arg Tyr Ala Ala Val Gln Gly Val Ala Ser Met Val Cys Phe Tyr
                245                 250                 255 gga gtt cct ctt ctg att gtc aac ggg ttc tta gtt ttg atc act tac    816
Gly Val Pro Leu Leu Ile Val Asn Gly Phe Leu Val Leu Ile Thr Tyr
            260                 265                 270 ttg cag cac acg cat cct tcc ctg cct cac tat gac tcg tct gag tgg    864
Leu Gln His Thr His Pro Ser Leu Pro His Tyr Asp Ser Ser Glu Trp
        275                 280                 285 gat tgg ttg agg gga gct ttg gcc acc gtt gac aga gac tac gga atc    912
Asp Trp Leu Arg Gly Ala Leu Ala Thr Val Asp Arg Asp Tyr Gly Ile
    290                 295                 300 ttg aac aag gtc ttc cac aat atc acg gac acg cac gtg gcg cat cac    960
Leu Asn Lys Val Phe His Asn Ile Thr Asp Thr His Val Ala His His
305                 310                 315                 320 ctg ttc tcg acc atg ccg cat tat cac gcg atg gaa gct acg aag gcg   1008
Leu Phe Ser Thr Met Pro His Tyr His Ala Met Glu Ala Thr Lys Ala
                325                 330                 335 ata aag ccg ata ctg gga gag tat tat cag ttc gat ggg acg ccg gtg   1056
Ile Lys Pro Ile Leu Gly Glu Tyr Tyr Gln Phe Asp Gly Thr Pro Val
            340                 345                 350 gtt aag gcg atg tgg agg gag gcg aag gag tgt atc tat gtg gaa ccg   1104
Val Lys Ala Met Trp Arg Glu Ala Lys Glu Cys Ile Tyr Val Glu Pro
        355                 360                 365 gac agg caa ggt gag aag aaa ggt gtg ttc tgg tac aac aat aag tta   1152
Asp Arg Gln Gly Glu Lys Lys Gly Val Phe Trp Tyr Asn Asn Lys Leu
    370                 375                 380 tga                                                               1155
```

<210> SEQ ID NO 2
<211> LENGTH: 384
<212> TYPE: PRT
<213> ORGANISM: Brassica napus

<400> SEQUENCE: 2

```
Met Gly Ala Gly Gly Arg Met Gln Val Ser Pro Pro Ser Lys Lys Ser
1               5                   10                  15

Glu Thr Asp Asn Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
```

```
                    85                  90                  95
Leu Thr Gly Val Trp Val Ile Ala His Glu Cys Asp His His Ala Phe
                100                 105                 110
Ser Asp Tyr Gln Trp Leu Asp Asp Thr Val Gly Leu Ile Phe His Ser
                115                 120                 125
Phe Leu Leu Val Pro Tyr Phe Ser Trp Lys Tyr Ser His Arg Arg His
            130                 135                 140
His Ser Asn Thr Gly Ser Leu Glu Arg Asp Glu Val Phe Val Pro Lys
145                 150                 155                 160
Lys Lys Ser Asp Ile Lys Trp Tyr Gly Lys Tyr Leu Asn Asn Pro Leu
                165                 170                 175
Gly Arg Thr Val Met Leu Thr Val Gln Phe Thr Leu Gly Trp Pro Leu
                180                 185                 190
Tyr Leu Ala Phe Asn Val Ser Gly Arg Pro Tyr Asp Gly Phe Ala
                195                 200                 205
Cys His Phe His Pro Asn Ala Pro Ile Tyr Asn Asp Arg Glu Arg Leu
            210                 215                 220
Gln Ile Tyr Ile Ser Asp Ala Gly Ile Leu Ala Val Cys Tyr Gly Leu
225                 230                 235                 240
Tyr Arg Tyr Ala Ala Val Gln Gly Val Ala Ser Met Val Cys Phe Tyr
                245                 250                 255
Gly Val Pro Leu Leu Ile Val Asn Gly Phe Leu Val Leu Ile Thr Tyr
                260                 265                 270
Leu Gln His Thr His Pro Ser Leu Pro His Tyr Asp Ser Ser Glu Trp
                275                 280                 285
Asp Trp Leu Arg Gly Ala Leu Ala Thr Val Asp Arg Asp Tyr Gly Ile
            290                 295                 300
Leu Asn Lys Val Phe His Asn Ile Thr Asp Thr His Val Ala His His
305                 310                 315                 320
Leu Phe Ser Thr Met Pro His Tyr His Ala Met Glu Ala Thr Lys Ala
                325                 330                 335
Ile Lys Pro Ile Leu Gly Glu Tyr Tyr Gln Phe Asp Gly Thr Pro Val
                340                 345                 350
Val Lys Ala Met Trp Arg Glu Ala Lys Glu Cys Ile Tyr Val Glu Pro
            355                 360                 365
Asp Arg Gln Gly Glu Lys Lys Gly Val Phe Trp Tyr Asn Asn Lys Leu
            370                 375                 380

<210> SEQ ID NO 3
<211> LENGTH: 1155
<212> TYPE: DNA
<213> ORGANISM: Brassica napus
<220> FEATURE:
<221> NAME/KEY: CDS
<222> LOCATION: (1)..(1155)

<400> SEQUENCE: 3 atg ggt gca ggt gga aga atg caa gtg tct cct ccc tcc aaa aag tct      48
Met Gly Ala Gly Gly Arg Met Gln Val Ser Pro Pro Ser Lys Lys Ser
1               5                   10                  15 gaa acc gac aac atc aag cgc gta ccc tgc gag aca ccg ccc ttc act      96
Glu Thr Asp Asn Ile Lys Arg Val Pro Cys Glu Thr Pro Pro Phe Thr
                20                  25                  30 gtc gga gaa ctc aag aaa gca atc cca ccg cac tgt ttc aaa cgc tcg     144
Val Gly Glu Leu Lys Lys Ala Ile Pro Pro His Cys Phe Lys Arg Ser
            35                  40                  45 atc cct cgc tct ttc tcc tac ctc atc tgg gac atc atc ata gcc tcc     192
```

-continued

| | | | | | | | | | | | | | | | |
|---|---|---|---|---|---|---|---|---|---|---|---|---|---|---|---|
| Ile | Pro | Arg | Ser | Phe | Ser | Tyr | Leu | Ile | Trp | Asp | Ile | Ile | Ala | Ser | |
| | 50 | | | | 55 | | | | 60 | | | | | | |

| tgc | ttc | tac | tac | gtc | gcc | acc | act | tac | ttc | cct | ctc | ctc | cct | cac | cct | 240 |
|---|---|---|---|---|---|---|---|---|---|---|---|---|---|---|---|---|
| Cys | Phe | Tyr | Tyr | Val | Ala | Thr | Thr | Tyr | Phe | Pro | Leu | Leu | Pro | His | Pro | |
| 65 | | | | | 70 | | | | | 75 | | | | | 80 | |

| ctc | tcc | tac | ttc | gcc | tgg | cct | ctc | tac | tgg | gcc | tgc | cag | ggc | tgc | gtc | 288 |
|---|---|---|---|---|---|---|---|---|---|---|---|---|---|---|---|---|
| Leu | Ser | Tyr | Phe | Ala | Trp | Pro | Leu | Tyr | Trp | Ala | Cys | Gln | Gly | Cys | Val | |
| | | | | | 85 | | | | | 90 | | | | | 95 | |

| cta | acc | ggc | gtc | tgg | gtc | ata | gcc | cac | gag | tgc | ggc | cac | cac | gcc | ttc | 336 |
|---|---|---|---|---|---|---|---|---|---|---|---|---|---|---|---|---|
| Leu | Thr | Gly | Val | Trp | Val | Ile | Ala | His | Glu | Cys | Gly | His | His | Ala | Phe | |
| | | | | 100 | | | | | 105 | | | | | 110 | | |

| agc | gac | tac | cag | tgg | ctg | gac | gac | acc | gtc | ggc | ctc | atc | ttc | cac | tcc | 384 |
|---|---|---|---|---|---|---|---|---|---|---|---|---|---|---|---|---|
| Ser | Asp | Tyr | Gln | Trp | Leu | Asp | Asp | Thr | Val | Gly | Leu | Ile | Phe | His | Ser | |
| | | | | 115 | | | | | 120 | | | | | 125 | | |

| ttc | ctc | ctc | gtc | cct | tac | ttc | tcc | tgg | aag | tac | agt | cat | cga | cgc | cac | 432 |
|---|---|---|---|---|---|---|---|---|---|---|---|---|---|---|---|---|
| Phe | Leu | Leu | Val | Pro | Tyr | Phe | Ser | Trp | Lys | Tyr | Ser | His | Arg | Arg | His | |
| | 130 | | | | | 135 | | | | | 140 | | | | | |

| cat | tcc | aac | act | ggc | tcc | ctc | gag | aga | gac | gaa | gtg | ttt | gtc | ccc | aag | 480 |
|---|---|---|---|---|---|---|---|---|---|---|---|---|---|---|---|---|
| His | Ser | Asn | Thr | Gly | Ser | Leu | Glu | Arg | Asp | Glu | Val | Phe | Val | Pro | Lys | |
| 145 | | | | | 150 | | | | | 155 | | | | | 160 | |

| aag | aag | tca | gac | atc | aag | tgg | tac | ggc | aag | tac | ctc | aac | aac | cct | ttg | 528 |
|---|---|---|---|---|---|---|---|---|---|---|---|---|---|---|---|---|
| Lys | Lys | Ser | Asp | Ile | Lys | Trp | Tyr | Gly | Lys | Tyr | Leu | Asn | Asn | Pro | Leu | |
| | | | | 165 | | | | | 170 | | | | | 175 | | |

| gga | cgc | acc | gtg | atg | tta | acg | gtt | cag | ttc | act | ctc | ggc | tgg | cct | ttg | 576 |
|---|---|---|---|---|---|---|---|---|---|---|---|---|---|---|---|---|
| Gly | Arg | Thr | Val | Met | Leu | Thr | Val | Gln | Phe | Thr | Leu | Gly | Trp | Pro | Leu | |
| | | | | 180 | | | | | 185 | | | | | 190 | | |

| tac | tta | gcc | ttc | aac | gtc | tcg | ggg | aga | cct | tac | gac | ggc | ggc | ttc | gct | 624 |
|---|---|---|---|---|---|---|---|---|---|---|---|---|---|---|---|---|
| Tyr | Leu | Ala | Phe | Asn | Val | Ser | Gly | Arg | Pro | Tyr | Asp | Gly | Gly | Phe | Ala | |
| | | | 195 | | | | | 200 | | | | | 205 | | | |

| tgc | cat | ttc | cac | ccc | aac | gct | ccc | atc | tac | aac | gac | cgt | gag | cgt | ctc | 672 |
|---|---|---|---|---|---|---|---|---|---|---|---|---|---|---|---|---|
| Cys | His | Phe | His | Pro | Asn | Ala | Pro | Ile | Tyr | Asn | Asp | Arg | Glu | Arg | Leu | |
| | | 210 | | | | | 215 | | | | | 220 | | | | |

| cag | ata | tac | atc | tcc | gac | gct | ggc | atc | ctc | gcc | gtc | tgc | tac | ggt | ctc | 720 |
|---|---|---|---|---|---|---|---|---|---|---|---|---|---|---|---|---|
| Gln | Ile | Tyr | Ile | Ser | Asp | Ala | Gly | Ile | Leu | Ala | Val | Cys | Tyr | Gly | Leu | |
| 225 | | | | | 230 | | | | | 235 | | | | | 240 | |

| tac | cgc | tac | gct | gct | gtc | caa | gga | gtt | gcc | tcg | atg | gtc | tgc | ttc | tac | 768 |
|---|---|---|---|---|---|---|---|---|---|---|---|---|---|---|---|---|
| Tyr | Arg | Tyr | Ala | Ala | Val | Gln | Gly | Val | Ala | Ser | Met | Val | Cys | Phe | Tyr | |
| | | | | 245 | | | | | 250 | | | | | 255 | | |

| gga | gtt | cct | ctt | ctg | att | gtc | aac | ggg | ttc | tta | gtt | ttg | atc | act | tac | 816 |
|---|---|---|---|---|---|---|---|---|---|---|---|---|---|---|---|---|
| Gly | Val | Pro | Leu | Leu | Ile | Val | Asn | Gly | Phe | Leu | Val | Leu | Ile | Thr | Tyr | |
| | | | | 260 | | | | | 265 | | | | | 270 | | |

| ttg | cag | cac | acg | cat | cct | tcc | ctg | cct | cac | tat | gac | tcg | tct | gag | tgg | 864 |
|---|---|---|---|---|---|---|---|---|---|---|---|---|---|---|---|---|
| Leu | Gln | His | Thr | His | Pro | Ser | Leu | Pro | His | Tyr | Asp | Ser | Ser | Glu | Trp | |
| | | 275 | | | | | 280 | | | | | 285 | | | | |

| gat | tgg | ttg | agg | gga | gct | ttg | gcc | acc | gtt | gac | aga | gac | tac | gga | atc | 912 |
|---|---|---|---|---|---|---|---|---|---|---|---|---|---|---|---|---|
| Asp | Trp | Leu | Arg | Gly | Ala | Leu | Ala | Thr | Val | Asp | Arg | Asp | Tyr | Gly | Ile | |
| | 290 | | | | | 295 | | | | | 300 | | | | | |

| ttg | aac | aag | gtc | ttc | cac | aat | atc | acg | gac | acg | cac | gtg | gcg | cat | cac | 960 |
|---|---|---|---|---|---|---|---|---|---|---|---|---|---|---|---|---|
| Leu | Asn | Lys | Val | Phe | His | Asn | Ile | Thr | Asp | Thr | His | Val | Ala | His | His | |
| 305 | | | | | 310 | | | | | 315 | | | | | 320 | |

| ctg | ttc | tcg | acc | atg | ccg | cat | tat | cac | gcg | atg | gaa | gct | acg | aag | gcg | 1008 |
|---|---|---|---|---|---|---|---|---|---|---|---|---|---|---|---|---|
| Leu | Phe | Ser | Thr | Met | Pro | His | Tyr | His | Ala | Met | Glu | Ala | Thr | Lys | Ala | |
| | | | | 325 | | | | | 330 | | | | | 335 | | |

| ata | aag | ccg | ata | ctg | gga | gag | tat | tat | cag | ttc | gat | ggg | acg | ccg | gtg | 1056 |
|---|---|---|---|---|---|---|---|---|---|---|---|---|---|---|---|---|
| Ile | Lys | Pro | Ile | Leu | Gly | Glu | Tyr | Tyr | Gln | Phe | Asp | Gly | Thr | Pro | Val | |
| | | | 340 | | | | | 345 | | | | | 350 | | | |

| gtt | aag | gcg | atg | tgg | agg | gag | gcg | aag | gag | tgt | atc | tat | gtg | gaa | ccg | 1104 |
|---|---|---|---|---|---|---|---|---|---|---|---|---|---|---|---|---|
| Val | Lys | Ala | Met | Trp | Arg | Glu | Ala | Lys | Glu | Cys | Ile | Tyr | Val | Glu | Pro | |
| | | 355 | | | | | 360 | | | | | 365 | | | | |

| gac | agg | caa | ggt | gag | aag | aaa | ggt | gtg | ttc | tgg | tac | aac | aat | aag | tta | 1152 |
|---|---|---|---|---|---|---|---|---|---|---|---|---|---|---|---|---|

Asp Arg Gln Gly Glu Lys Lys Gly Val Phe Trp Tyr Asn Asn Lys Leu
370                 375                 380 tga                                                                                    1155

<210> SEQ ID NO 4
<211> LENGTH: 384
<212> TYPE: PRT
<213> ORGANISM: Brassica napus

<400> SEQUENCE: 4

Met Gly Ala Gly Gly Arg Met Gln Val Ser Pro Pro Ser Lys Lys Ser
1               5                   10                  15

Glu Thr Asp Asn Ile Lys Arg Val Pro Cys Glu Thr Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Phe Ala
        195                 200                 205

Cys His Phe His Pro Asn Ala Pro Ile Tyr Asn Asp Arg Glu Arg Leu
210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro

```
               355                 360                 365
Asp Arg Gln Gly Glu Lys Lys Gly Val Phe Trp Tyr Asn Asn Lys Leu
        370                 375                 380

<210> SEQ ID NO 5
<211> LENGTH: 1155
<212> TYPE: DNA
<213> ORGANISM: Brassica napus
<220> FEATURE:
<221> NAME/KEY: CDS
<222> LOCATION: (1)..(1155)

<400> SEQUENCE: 5 atg ggt gca ggt gga aga atg caa gtg tct cct ccc tcc aag aag tct      48
Met Gly Ala Gly Gly Arg Met Gln Val Ser Pro Pro Ser Lys Lys Ser
1               5                   10                  15 gaa acc gac acc atc aag cgc gta ccc tgc gag aca ccg ccc ttc act      96
Glu Thr Asp Thr Ile Lys Arg Val Pro Cys Glu Thr Pro Pro Phe Thr
            20                  25                  30 gtc gga gaa ctc aag aaa gca atc cca ccg cac tgt ttc aaa cgc tcg     144
Val Gly Glu Leu Lys Lys Ala Ile Pro Pro His Cys Phe Lys Arg Ser
        35                  40                  45 atc cct cgc tct ttc tcc tac ctc atc tgg gac atc ata gcc tcc         192
Ile Pro Arg Ser Phe Ser Tyr Leu Ile Trp Asp Ile Ile Ala Ser
    50                  55                  60 tgc ttc tac tac gtc gcc acc act tac ttc cct ctc ctc cct cac cct     240
Cys Phe Tyr Tyr Val Ala Thr Thr Tyr Phe Pro Leu Leu Pro His Pro
65                  70                  75                  80 ctc tcc tac ttc gcc tgg cct ctc tac tgg gcc tgc caa ggg tgc gtc     288
Leu Ser Tyr Phe Ala Trp Pro Leu Tyr Trp Ala Cys Gln Gly Cys Val
                85                  90                  95 cta acc ggc gtc tgg gtc ata gcc cac gag tgc ggc cac cac gcc ttc     336
Leu Thr Gly Val Trp Val Ile Ala His Glu Cys Gly His His Ala Phe
            100                 105                 110 agc gac tac cag tgg ttt gac gac acc gtc ggt ctc atc ttc cac tcc     384
Ser Asp Tyr Gln Trp Phe Asp Asp Thr Val Gly Leu Ile Phe His Ser
        115                 120                 125 ttc ctc ctc gtc cct tac ttc tcc tgg aag tac agt cat cga cgc cac     432
Phe Leu Leu Val Pro Tyr Phe Ser Trp Lys Tyr Ser His Arg Arg His
    130                 135                 140 cat tcc aac act ggc tcc ctc gag aga gac gaa gtg ttt gtc ccc aag     480
His Ser Asn Thr Gly Ser Leu Glu Arg Asp Glu Val Phe Val Pro Lys
145                 150                 155                 160 aag aag tca gac atc aag tgg tac ggc aag tac ctc aac aac cct ttg     528
Lys Lys Ser Asp Ile Lys Trp Tyr Gly Lys Tyr Leu Asn Asn Pro Leu
                165                 170                 175 gga cgc acc gtg atg tta acg gtt cag ttc act ctc ggc tgg ccg ttg     576
Gly Arg Thr Val Met Leu Thr Val Gln Phe Thr Leu Gly Trp Pro Leu
            180                 185                 190 tac tta gcc ttc aac gtc tcg gga aga cct tac gac ggc ggc ttc gct     624
Tyr Leu Ala Phe Asn Val Ser Gly Arg Pro Tyr Asp Gly Gly Phe Ala
        195                 200                 205 tgc cat ttc cac ccc aac gct ccc atc tac aac gac cgc gag cgt ctc     672
Cys His Phe His Pro Asn Ala Pro Ile Tyr Asn Asp Arg Glu Arg Leu
    210                 215                 220 cag ata tac atc tcc gac gct ggc atc ctc gcc gtc tgc tac ggt ctc     720
Gln Ile Tyr Ile Ser Asp Ala Gly Ile Leu Ala Val Cys Tyr Gly Leu
225                 230                 235                 240 ttc cgt tac gcc gcc gcg cag gga gtg gcc tcg atg gtc tgc ttc tac     768
Phe Arg Tyr Ala Ala Ala Gln Gly Val Ala Ser Met Val Cys Phe Tyr
                245                 250                 255
```

```
gga gtc ccg ctt ctg att gtc aat ggt ttc ctc gtg ttg atc act tac        816
Gly Val Pro Leu Leu Ile Val Asn Gly Phe Leu Val Leu Ile Thr Tyr
        260                 265                 270 ttg cag cac acg cat cct tcc ctg cct cac tac gat tcg tcc gag tgg        864
Leu Gln His Thr His Pro Ser Leu Pro His Tyr Asp Ser Ser Glu Trp
        275                 280                 285 gat tgg ttg agg gga gct ttg gct acc gtt gac aga gac tac gga atc        912
Asp Trp Leu Arg Gly Ala Leu Ala Thr Val Asp Arg Asp Tyr Gly Ile
        290                 295                 300 ttg aac aag gtc ttc cac aat att acc gac acg cac gtg gcg cat cat        960
Leu Asn Lys Val Phe His Asn Ile Thr Asp Thr His Val Ala His His
305                 310                 315                 320 ctg ttc tcc acg atg ccg cat tat cac gcg atg gaa gct acc aag gcg       1008
Leu Phe Ser Thr Met Pro His Tyr His Ala Met Glu Ala Thr Lys Ala
                325                 330                 335 ata aag ccg ata ctg gga gag tat tat cag ttc gat ggg acg ccg gtg       1056
Ile Lys Pro Ile Leu Gly Glu Tyr Tyr Gln Phe Asp Gly Thr Pro Val
        340                 345                 350 gtt aag gcg atg tgg agg gag gcg aag gag tgt atc tat gtg gaa ccg       1104
Val Lys Ala Met Trp Arg Glu Ala Lys Glu Cys Ile Tyr Val Glu Pro
        355                 360                 365 gac agg caa ggt gag aag aaa ggt gtg ttc tgg tac aac aat aag tta       1152
Asp Arg Gln Gly Glu Lys Lys Gly Val Phe Trp Tyr Asn Asn Lys Leu
        370                 375                 380 tga                                                                    1155

<210> SEQ ID NO 6
<211> LENGTH: 384
<212> TYPE: PRT
<213> ORGANISM: Brassica napus

<400> SEQUENCE: 6

Met Gly Ala Gly Gly Arg Met Gln Val Ser Pro Pro Ser Lys Lys Ser
1               5                   10                  15

Glu Thr Asp Thr Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Phe Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205
```

```
Cys His Phe His Pro Asn Ala Pro Ile Tyr Asn Asp Arg Glu Arg Leu
        210                 215                 220

Gln Ile Tyr Ile Ser Asp Ala Gly Ile Leu Ala Val Cys Tyr Gly Leu
225                 230                 235                 240

Phe Arg Tyr Ala Ala Gln Gly Val Ala Ser Met Val Cys Phe Tyr
                245                 250                 255

Gly Val Pro Leu Leu Ile Val Asn Gly Phe Leu Val Leu Ile Thr Tyr
                260                 265                 270

Leu Gln His Thr His Pro Ser Leu Pro His Tyr Asp Ser Ser Glu Trp
            275                 280                 285

Asp Trp Leu Arg Gly Ala Leu Ala Thr Val Asp Arg Asp Tyr Gly Ile
            290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
            355                 360                 365

Asp Arg Gln Gly Glu Lys Lys Gly Val Phe Trp Tyr Asn Asn Lys Leu
370                 375                 380

<210> SEQ ID NO 7
<211> LENGTH: 1155
<212> TYPE: DNA
<213> ORGANISM: Brassica napus
<220> FEATURE:
<221> NAME/KEY: CDS
<222> LOCATION: (1)..(1155)

<400> SEQUENCE: 7 atg ggt gca ggt gga aga atg caa gtg tct cct ccc tcc aag aag tct      48
Met Gly Ala Gly Gly Arg Met Gln Val Ser Pro Pro Ser Lys Lys Ser
1               5                   10                  15 gaa acc gac acc atc aag cgc gta ccc tgc gag aca ccg ccc ttc act      96
Glu Thr Asp Thr Ile Lys Arg Val Pro Cys Glu Thr Pro Pro Phe Thr
                20                  25                  30 gtc gga gaa ctc aag aaa gca atc cca ccg cac tgt ttc aaa cgc tcg     144
Val Gly Glu Leu Lys Lys Ala Ile Pro Pro His Cys Phe Lys Arg Ser
            35                  40                  45 atc cct cgc tct ttc tcc tac ctc atc tgg gac atc atc ata gcc tcc     192
Ile Pro Arg Ser Phe Ser Tyr Leu Ile Trp Asp Ile Ile Ile Ala Ser
        50                  55                  60 tgc ttc tac tac gtc gcc acc act tac ttc cct ctc ctc cct cac cct     240
Cys Phe Tyr Tyr Val Ala Thr Thr Tyr Phe Pro Leu Leu Pro His Pro
65                  70                  75                  80 ctc tcc tac ttc gcc tgg cct ctc tac tgg gcc tgc caa ggg tgc gtc     288
Leu Ser Tyr Phe Ala Trp Pro Leu Tyr Trp Ala Cys Gln Gly Cys Val
                85                  90                  95 cta acc ggc gtc tgg gtc ata gcc cac gag tgc ggc cac cac gcc ttc     336
Leu Thr Gly Val Trp Val Ile Ala His Glu Cys Gly His His Ala Phe
            100                 105                 110 agc gac tac cag tgg ctt gac gac acc gtc ggt ctc atc ttc cac tcc     384
Ser Asp Tyr Gln Trp Leu Asp Asp Thr Val Gly Leu Ile Phe His Ser
        115                 120                 125 ttc ctc ctc gtc cct tac ttc tcc tgg aag tac agt cat cga cgc cac     432
Phe Leu Leu Val Pro Tyr Phe Ser Trp Lys Tyr Ser His Arg Arg His
130                 135                 140
```

```
cat tcc aac act ggc tcc ctc gag aga gac gaa gtg ttt gtc ccc aag    480
His Ser Asn Thr Gly Ser Leu Glu Arg Asp Glu Val Phe Val Pro Lys
145                 150                 155                 160 aag aag tca gac atc aag tgg tac ggc aag tac ctc aac aac cct ttg    528
Lys Lys Ser Asp Ile Lys Trp Tyr Gly Lys Tyr Leu Asn Asn Pro Leu
                165                 170                 175 gga cgc acc gtg atg tta acg gtt cag ttc act ctc ggc tgg ccg ttg    576
Gly Arg Thr Val Met Leu Thr Val Gln Phe Thr Leu Gly Trp Pro Leu
            180                 185                 190 tac tta gcc ttc aac gtc tcg gga aga cct tac gac ggc ggc ttc gct    624
Tyr Leu Ala Phe Asn Val Ser Gly Arg Pro Tyr Asp Gly Gly Phe Ala
        195                 200                 205 tgc cat ttc cac ccc aac gct ccc atc tac aac gac cgc gag cgt ctc    672
Cys His Phe His Pro Asn Ala Pro Ile Tyr Asn Asp Arg Glu Arg Leu
    210                 215                 220 cag ata tac atc tcc gac gct ggc atc ctc gcc gtc tgc tac ggt ctc    720
Gln Ile Tyr Ile Ser Asp Ala Gly Ile Leu Ala Val Cys Tyr Gly Leu
225                 230                 235                 240 ttc cgt tac gcc gcc gcg cag gga gtg gcc tcg atg gtc tgc ttc tac    768
Phe Arg Tyr Ala Ala Ala Gln Gly Val Ala Ser Met Val Cys Phe Tyr
                245                 250                 255 gga gtc ccg ctt ctg att gtc aat ggt ttc ctc gtg ttg atc act tac    816
Gly Val Pro Leu Leu Ile Val Asn Gly Phe Leu Val Leu Ile Thr Tyr
            260                 265                 270 ttg cag cac acg cat cct tcc ctg cct cac tac gat tcg tcc gag tgg    864
Leu Gln His Thr His Pro Ser Leu Pro His Tyr Asp Ser Ser Glu Trp
        275                 280                 285 gat tgg ttg agg gga gct ttg gct acc gtt gac aga gac tac gga atc    912
Asp Trp Leu Arg Gly Ala Leu Ala Thr Val Asp Arg Asp Tyr Gly Ile
    290                 295                 300 ttg aac aag gtc ttc cac aat att acc gac acg cac gtg gcg cat cat    960
Leu Asn Lys Val Phe His Asn Ile Thr Asp Thr His Val Ala His His
305                 310                 315                 320 ctg ttc tcc acg atg ccg cat tat cac gcg atg gaa gct acc aag gcg   1008
Leu Phe Ser Thr Met Pro His Tyr His Ala Met Glu Ala Thr Lys Ala
                325                 330                 335 ata aag ccg ata ctg gga gag tat tat cag ttc gat ggg acg ccg gtg   1056
Ile Lys Pro Ile Leu Gly Glu Tyr Tyr Gln Phe Asp Gly Thr Pro Val
            340                 345                 350 gtt aag gcg atg tgg agg gag gcg aag gag tgt atc tat gtg gaa ccg   1104
Val Lys Ala Met Trp Arg Glu Ala Lys Glu Cys Ile Tyr Val Glu Pro
        355                 360                 365 gac agg caa ggt gag aag aaa ggt gtg ttc tgg tac aac aat aag tta   1152
Asp Arg Gln Gly Glu Lys Lys Gly Val Phe Trp Tyr Asn Asn Lys Leu
    370                 375                 380 tga                                                                1155

<210> SEQ ID NO 8
<211> LENGTH: 384
<212> TYPE: PRT
<213> ORGANISM: Brassica napus

<400> SEQUENCE: 8

Met Gly Ala Gly Gly Arg Met Gln Val Ser Pro Pro Ser Lys Lys Ser
1               5                   10                  15

Glu Thr Asp Thr Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45
```

-continued

```
Ile Pro Arg Ser Phe Ser Tyr Leu Ile Trp Asp Ile Ile Ala Ser
    50                  55                  60
Cys Phe Tyr Tyr Val Ala Thr Thr Tyr Phe Pro Leu Leu Pro His Pro
 65                  70                  75                  80
Leu Ser Tyr Phe Ala Trp Pro Leu Tyr Trp Ala Cys Gln Gly Cys Val
                 85                  90                  95
Leu Thr Gly Val Trp Val Ile Ala His Glu Cys Gly His His Ala Phe
                100                 105                 110
Ser Asp Tyr Gln Trp Leu Asp Asp Thr Val Gly Leu Ile Phe His Ser
                115                 120                 125
Phe Leu Leu Val Pro Tyr Phe Ser Trp Lys Tyr Ser His Arg Arg His
130                 135                 140
His Ser Asn Thr Gly Ser Leu Glu Arg Asp Glu Val Phe Val Pro Lys
145                 150                 155                 160
Lys Lys Ser Asp Ile Lys Trp Tyr Gly Lys Tyr Leu Asn Asn Pro Leu
                165                 170                 175
Gly Arg Thr Val Met Leu Thr Val Gln Phe Thr Leu Gly Trp Pro Leu
                180                 185                 190
Tyr Leu Ala Phe Asn Val Ser Gly Arg Pro Tyr Asp Gly Gly Phe Ala
                195                 200                 205
Cys His Phe His Pro Asn Ala Pro Ile Tyr Asn Asp Arg Glu Arg Leu
                210                 215                 220
Gln Ile Tyr Ile Ser Asp Ala Gly Ile Leu Ala Val Cys Tyr Gly Leu
225                 230                 235                 240
Phe Arg Tyr Ala Ala Ala Gln Gly Val Ala Ser Met Val Cys Phe Tyr
                245                 250                 255
Gly Val Pro Leu Leu Ile Val Asn Gly Phe Leu Val Leu Ile Thr Tyr
                260                 265                 270
Leu Gln His Thr His Pro Ser Leu Pro His Tyr Asp Ser Ser Glu Trp
                275                 280                 285
Asp Trp Leu Arg Gly Ala Leu Ala Thr Val Asp Arg Asp Tyr Gly Ile
                290                 295                 300
Leu Asn Lys Val Phe His Asn Ile Thr Asp Thr His Val Ala His His
305                 310                 315                 320
Leu Phe Ser Thr Met Pro His Tyr His Ala Met Glu Ala Thr Lys Ala
                325                 330                 335
Ile Lys Pro Ile Leu Gly Glu Tyr Tyr Gln Phe Asp Gly Thr Pro Val
                340                 345                 350
Val Lys Ala Met Trp Arg Glu Ala Lys Glu Cys Ile Tyr Val Glu Pro
                355                 360                 365
Asp Arg Gln Gly Glu Lys Lys Gly Val Phe Trp Tyr Asn Asn Lys Leu
370                 375                 380
```

<210> SEQ ID NO 9
<211> LENGTH: 1561
<212> TYPE: DNA
<213> ORGANISM: Brassica napus

<400> SEQUENCE: 9

```
gagaaccaga gagattcatt accaaagaga tagagagaga gagaaagaga ggagacagag      60
agagagtttg aggaggagct tcttcgtagg gttcatcgtt attaacgtta aatcttcatc     120
cccccctacg tcagccagct caagaaacat gggtgcaggt ggaagaatgc aagtgtctcc     180
tccctccaaa aagtctgaaa ccgacaacat caagcgcgta ccctgcgaga caccgccctt     240
cactgtcgga gaactcaaga agcaatccc accgcactgt ttcaaacgct cgatccctcg      300
```

```
ctctttctcc tacctcatct gggacatcat catagcctcc tgcttctact acgtcgccac    360
cacttacttc cctctcctcc ctcaccctct ctcctacttc gcctggcctc tctactgggc    420
ctgccagggc tgcgtcctaa ccggcgtctg ggtcatagcc cacgagtgcg gccaccacgc    480
cttcagcgac taccagtggc tggacgacac cgtcggcctc atcttccact ccttcctcct    540
cgtcccttac ttctcctgga agtacagtca tcgacgccac cattccaaca ctggctccct    600
cgagagagac gaagtgtttg tccccaagaa gaagtcagac atcaagtggt acggcaagta    660
cctcaacaac cctttgggac gcaccgtgat gttaacggtt cagttcactc tcggctggcc    720
tttgtactta gccttcaacg tctcggggag accttacgac ggcggcttcg cttgccattt    780
ccaccccaac gctcccatct acaacgaccg tgagcgtctc cagatataca tctccgacgc    840
tggcatcctc gccgtctgct acggtctcta ccgctacgct gctgtccaag gagttgcctc    900
gatggtctgc ttctacggag ttcctcttct gattgtcaac gggttcttag ttttgatcac    960
ttacttgcag cacacgcatc cttccctgcc tcactatgac tcgtctgagt gggattggtt   1020
gaggggagct ttggccaccg ttgacagaga ctacggaatc ttgaacaagg tcttccacaa   1080
tatcacggac acgcacgtgg cgcatcacct gttctcgacc atgccgcatt atcatgcgat   1140
ggaagctacg aaggcgataa agccgatact gggagagtat tatcagttcg atgggacgcc   1200
ggtggttaag gcgatgtgga gggaggcgaa ggagtgtatc tatgtggaac cggacaggca   1260
aggtgagaag aaaggtgtgt tctggtacaa caataagtta tgaagcaaag aagaaactga   1320
acctttctcw tcctatgatt gtctttgttt aagaagctat gtttctgttt caataatctt   1380
taattatcca ttttgttgtg ttttctgaca ttttggctaa aattatgtga tgttggaagt   1440
tagtgtctaa aatgtcttgt gtctgtattg ttcttcttct catcgctgtt atgtttggga   1500
tcgttgaaat gtgactttcg gactagtgaa ctcttgttct cgaactaaaa aaaaaaaaaa   1560
a                                                                   1561

<210> SEQ ID NO 10
<211> LENGTH: 1553
<212> TYPE: DNA
<213> ORGANISM: Brassica napus

<400> SEQUENCE: 10
gagacagatt cattaccaaa gagatagaga aagagagaga gagagagaga gagagagagt     60
gagtttgagg aggagcttct tcgtagggtt catcgttatt aacgttaaat cttcaccccc    120
tacgtcagcc agctcaagaa acatgggtgc aggtggaaga atgcaagtgt ctcctccctc    180
caagaagtct gaaaccgaca ccatcaagcg cgtaccctgc gagacaccgc ccttcactgt    240
cggagaactc aagaaagcaa tcccaccgca ctgtttcaaa cgctcgatcc ctcgctcttt    300
ctcctacctc atctgggaca tcatcatagc ctcctgcttc tactacgtcg ccaccactta    360
cttccctctc ctccctcacc ctctctccta cttcgcctgg cctctctact gggcctgcca    420
agggtgcgtc ctaaccggcg tctgggtcat agcccacgag tgcggccacc acgccttcag    480
cgactaccag tggcttgacg acaccgtcgg tctcatcttc cactccttcc tctcgtccc    540
ttacttctcc tggaagtaca gtcatcgacg ccaccattcc aacactggct ccctcgagag    600
agacgaagtg tttgtcccca agaagaagtc agacatcaag tggtacggca agtacctcaa    660
caaccctttg ggacgcaccg tgatgttaac ggttcagttc actctcggct ggccgttgta    720
cttagccttc aacgtctcgg gaagacctta cgacggcggc ttcgcttgcc atttccaccc    780
caacgctccc atctacaacg accgcgagcg tctccagata tacatctccg acgctggcat    840
```

```
cctcgccgtc tgctacggtc tcttccgtta cgccgccgss cagggagtgg cctcgatggt      900
ctgcttctac ggagtcccgc ttctgattgt caatggtttc ctcgtgttga tcacttactt      960
gcagcacacg catccttccc tgcctcacta cgattcgtcc gagtgggatt ggttsagggg     1020
agctttggct accgttgaca gagactacgg aatcttgaac aaggtcttcc acaatattac     1080
cgacacgcac gtggcscatc atcygttctc cacgatgccg cattatcacg cgatggaagc     1140
taccaaggcg ataaagccga tactgggaga gtattatcag ttcgatggga cgccggtggt     1200
taaggcgatg tggagggagg cgaaggagtg tatctatgtg gaaccggaca ggcaaggtga     1260
gaagaaaggt gtgttctggt acaacaataa gttatgagga trraagaaac tgaacctttc     1320
tcttcctatg attgtctttg tttaagaagc tatgttctg tttcaataat cttaattatc      1380
cattttgttg tgttttctga cattttggct aaaattatgt gatgttggaa gttagtgtct     1440
aaaatgtctt gtgtctgtat tgttcttctt ctcatcgctg ttatgtttgg gatcgttgaa     1500
atgtgacttt cggactagtg aactcttgtt ctcgaactaa aaaaaaaaaa aaa            1553

<210> SEQ ID NO 11
<211> LENGTH: 2614
<212> TYPE: DNA
<213> ORGANISM: Brassica napus

<400> SEQUENCE: 11
agagagagaa gagaggagac agagagagag tttgaggagg agcttcttcg tagggttcat       60
cgttattaac gttaaatctt catcccccc tacgtcagcc agctcaaggt cccttcttc       120 ttccatttct tctcattttt acgttgtttt caatcttggt ctgttctttt cttatcgctt      180
ttctgttcta tctatcattt ttgcatttca gtcgatttat ttctagatct gttaatattt      240
attgcattaa actatagatc tggtcttgat tctctgtttt catgtgtgaa atcttgatgc      300
tgtcttaacc attaatctga ttatattgtc tataccgtgg agaatatgaa atgttgcatt      360
ttcatttgtc cgaatacaaa ctgtttgact ttcaatcgtt tttaaaatta tatatatatt      420
tttgatgggt tggtggagtt gaaaaatcac catagcagtc tcacgtcctg gtcttagaaa      480
tatccttcct attcaaagtt atatatattt gtttacttt gttttagatc tggacctgag      540
acatgtaagt acatatttgt tgaatctttg ggtaaaaaac ttatgtctct gggtaaaatt      600
tgctgagaga tttgaccgat tcctattggc tctggattct gtagttacct aatacatgaa      660
aaagtttcat ttggcctatg ctcacttcat gcttataaac ttttttcttgc aaattaattg     720 gattagatgc tccttcatag attcagatgc aatagatttg catgaagaaa ataataggat      780
tcatgatagt aaaaagagatt gtattttgt ttgtttgtt atgttaaaa gtctatatgt       840 tgacaataga gttgctatca actgtttcat ttaggtttat gttttgtca agttgcttat       900 tctaagagac attgtgatta tgacttgtct tctctaacgt agtttagtaa taaaagacga      960
aagaaattga tatccacaag aaagagatgt aagctgtaac gtatcaaatc tcattaataa     1020
ctagtagtat tctcaacgct atcgtttatt tctttctttg gtttgccact atatgccgct     1080
tctctgctct tttatcccac gtactatcca ttttttttgt ggtagtccat tttttgaaa      1140 ctttaataac gtaacactga atattaattt gttggtttaa ttaactttga gtctttgctt     1200
ttggtttatg cagaaacatg ggtgcaggtg gaagaatgca agtgtctcct ccctccaaaa     1260
agtctgaaac cgacaacatc aagcgcgtac cctgcgagac accgcccttc actgtcggag     1320
aactcaagaa agcaatccca ccgcactgtt tcaaacgctc gatccctcgc tctttctcct     1380
acctcatctg ggacatcatc atagcctcct gcttctacta cgtcgccacc acttacttcc     1440
```

```
ctctcctccc tcaccctctc tcctacttcg cctggcctct ctactgggcc tgccagggct      1500
gcgtcctaac cggcgtctgg gtcatagccc acgagtgcga ccaccacgcc ttcagcgact      1560
accagtggct ggacgacacc gtcggcctca tcttccactc cttcctcctc gtcccttact      1620
tctcctggaa gtacagtcat cgacgccacc attccaacac tggctccctc gagagagacg      1680
aagtgtttgt ccccaagaag aagtcagaca tcaagtggta cggcaagtac ctcaacaacc      1740
ctttgggacg caccgtgatg ttaacggttc agttcactct cggctggcct ttgtacttag      1800
ccttcaacgt ctcggggaga ccttacgacg gcggcttcgc ttgccatttc caccccaacg      1860
ctcccatcta caacgaccgt gagcgtctcc agatatacat ctccgacgct ggcatcctcg      1920
ccgtctgcta cggtctctac cgctacgctg ctgtccaagg agttgcctcg atggtctgct      1980
tctacggagt cctcttctg attgtcaacg ggttcttagt tttgatcact tacttgcagc       2040
acacgcatcc ttccctgcct cactatgact cgtctgagtg ggattggttg aggggagctt      2100
tggccaccgt tgacagagac tacgaatct tgaacaaggt cttccacaat atcacggaca       2160
cgcacgtggc gcatcacctg ttctcgacca tgccgcatta tcacgcgatg gaagctacga      2220
aggcgataaa gccgatactg ggagagtatt atcagttcga tgggacgccg gtggttaagg      2280
cgatgtggag ggaggcgaag gagtgtatct atgtggaacc ggacaggcaa ggtgagaaga      2340
aaggtgtgtt ctggtacaac aataagttat gaagcaaaga agaaactgaa cctttctcat      2400
ctatgattgt ctttgtttta agaagctatg tttctgtttc aataatcttt aattatccat      2460
tttgttgtgt tttctgacat tttggctaaa attatgtgat gttggaagtt agtgtctaaa      2520
atgtcttgtg tctgtattgt tcttcttctc atcgctgtta tgtttgggat cgttgaaatg      2580
tgactttcgg actagtgaat cttgttctcg aact                                  2614

<210> SEQ ID NO 12
<211> LENGTH: 2666
<212> TYPE: DNA
<213> ORGANISM: Brassica napus

<400> SEQUENCE: 12
gagaagagag agagagagag agagagagag agtgagtttg aggaggagct tcttcgtagg        60
gttcatcgtt attaacgtta aatcttcacc ccctacgtca gccagctcaa ggtccctttc      120
ttcttccatt tctttcatt ctacgttgtt ttcaatctta tgaaactttc tggtctgtgc       180
ttttcttatc gcttttctat tctatctatc attttttgcat ttcagtcgat ttaattctag     240
atctgttaat attaaactat agatctgttc ttgattctct gttttcatgt gtgaaatctg      300
atgctgtatt aatctgatta tattgtctat accgtggaga atatcaaatg ttgcattttc      360
atttgtccga atacaaagtg tttgactttc aatcgttttt aattatatat atatatatat      420 ttttgatgg gttggtggag ttgaaaaatc accatagcag tctcacgtcc tggttttaga       480
aatatcctat tcaaaattat atatttgttt acttgtttta gatctggacc tgagacatat      540
aagtacctat tgttgaatc tttgggtaaa aacttatgtc tctgggtaaa atttgctggg       600
agatttgacc gattcctatt ggctcttgat tctgtagtta cgtaatacat gaaaaagttt      660
catttggcct atgctcactt catgcttata aacgttttct tgcaaattaa ttggattaga      720
tgttatttca tagattcagt cattcagata caatggagtt gcatgaagaa ataatagaa       780 ttcgtgacag taaaaaagat tgtattttg tttgtttgtt tatgtttaaa agtctatatg       840
ttgacaatag agttgctctc aactgtttca tttagcttct ttttttgtca agttgcttat      900
tcttagagac attgtgatta tgacttgtct tctttaacgt agtttagtaa taaaagacga      960
```

-continued

```
aagaaattga tatccacaag aaagagatgt gagctgtagc gtatcaaatc tcgttcattt      1020
actagtagta ttctcaacgc tatcgtttat ttatttttct ttcgttggtt tgccactata      1080
tgccacttct ctcctctttg tcccacgtac tatccatttt ttttgtggta gtccattttc      1140
ttgtaactta taataacgta actctgaatc ttttgtctgt agattaattt gttggtttaa      1200
ttaactttta agtctttgct tttggcttat gcagaaacat gggtgcaggt ggaagaatgc      1260
aagtgtctcc tccctccaag aagtctgaaa ccgacaccat caagcgcgta ccctgcgaga      1320
caccgccctt cactgtcgga gaactcaaga aagcaatccc accgcactgt ttcaaacgct      1380
cgatccctcg ctctttctcc tacctcatct gggacatcat catagcctcc tgcttctact      1440
acgtcgccac cacttacttc cctctcctcc ctcaccctct ctcctacttc gcctggcctc      1500
tctactgggc ctgccaaggg tgcgtcctaa ccggcgtctg ggtcatagcc cacgagtgcg      1560
gccaccacgc cttcagcgac taccagtggt ttgacgacac cgtcggtctc atcttccact      1620
ccttcctcct cgtcccttac ttctcctgga agtacagtca tcgacgccac cattccaaca      1680
ctggctccct cgagagagac gaagtgtttg tccccaagaa gaagtcagac atcaagtggt      1740
acggcaagta cctcaacaac cctttgggac gcaccgtgat gttaacggtt cagttcactc      1800
tcggctggcc gttgtactta gccttcaacg tctcgggaag accttacgac ggcggcttcg      1860
cttgccattt ccaccccaac gctcccatct acaacgaccg cgagcgtctc cagatataca      1920
tctccgacgc tggcatcctc gccgtctgct acggtctctt ccgttacgcc gccgcgcagg      1980
gagtggcctc gatggtctgc ttctacggag tcccgcttct gattgtcaat ggtttcctcg      2040
tgttgatcac ttacttgcag cacacgcatc cttccctgcc tcactacgat tcgtccgagt      2100
gggattggtt gaggggagct ttggctaccg ttgacagaga ctacggaatc ttgaacaagg      2160
tcttccacaa tattaccgac acgcacgtgg cgcatcatct gttctccacg atgccgcatt      2220
atcacgcgat ggaagctacc aaggcgataa agccgatact gggagagtat tatcagttcg      2280
atgggacgcc ggtggttaag gcgatgtgga gggaggcgaa ggagtgtatc tatgtggaac      2340
cggacaggca aggtgagaag aaaggtgtgt tctggtacaa caataagtta tgaggatatg      2400
atgatggtga aagaacaaag aagatattgt cacgaaccct tctcttgctg tctctggtcg      2460
tctttgtttt aagaagctat gttttcgttt caataatctt aactatccat tttgttgtgt      2520
tttctgacat tttggctaaa attatgtgat gttggaagtt agtgtctaaa atgtcttgtg      2580
tctgtattgt tcttcttctc atcgctgtta tgtttgggat cgttgaaatg tgactttcgg      2640
actagtgaac tcttggttct cgaact                                           2666
```